(12) United States Patent
Struble et al.

(10) Patent No.: US 8,756,020 B2
(45) Date of Patent: Jun. 17, 2014

(54) ENHANCED RISK PROBABILITIES USING BIOMOLECULE ESTIMATIONS

(75) Inventors: Craig Struble, Glendale, WI (US); Eric Wang, Milpitas, CA (US); Andrew Sparks, San Jose, CA (US); Arnold Oliphant, San Jose, CA (US)

(73) Assignee: Ariosa Diagnostics, Inc., San Jose, CA (US)

( * ) Notice: Subject to any disclaimer, the term of this patent is extended or adjusted under 35 U.S.C. 154(b) by 234 days.

(21) Appl. No.: 13/274,309

(22) Filed: Oct. 15, 2011

(65) Prior Publication Data

US 2012/0190018 A1 Jul. 26, 2012

Related U.S. Application Data

(60) Provisional application No. 61/436,135, filed on Jan. 25, 2011.

(51) Int. Cl.
*G01N 33/50* (2006.01)

(52) U.S. Cl.
USPC .......................................................... 702/19

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,988,617 A | 1/1991 | Landegren et al. |
| 5,143,854 A | 9/1992 | Pirrung et al. |
| 5,242,794 A | 9/1993 | Whiteley et al. |
| 5,270,184 A | 12/1993 | Walker et al. |
| 5,399,491 A | 3/1995 | Kacian et al. |
| 5,409,818 A | 4/1995 | Davey et al. |
| 5,413,909 A | 5/1995 | Bassam et al. |
| 5,422,252 A | 6/1995 | Walker et al. |
| 5,437,975 A | 8/1995 | McClelland |
| 5,494,810 A | 2/1996 | Barany et al. |
| 5,547,839 A | 8/1996 | Dower et al. |
| 5,554,517 A | 9/1996 | Davey et al. |
| 5,578,832 A | 11/1996 | Trulson et al. |
| 5,631,734 A | 5/1997 | Stern et al. |
| 5,648,245 A | 7/1997 | Fire et al. |
| 5,800,992 A | 9/1998 | Fodor et al. |
| 5,808,041 A | 9/1998 | Padhye et al. |
| 5,830,711 A | 11/1998 | Barany et al. |
| 5,834,758 A | 11/1998 | Trulson et al. |
| 5,856,092 A | 1/1999 | Dale et al. |
| 5,861,245 A | 1/1999 | McClelland et al. |
| 5,871,928 A | 2/1999 | Fodor et al. |
| 5,874,219 A | 2/1999 | Rava et al. |
| 5,876,924 A | 2/1999 | Zhang et al. |
| 5,888,740 A | 3/1999 | Han |
| 5,898,071 A | 4/1999 | Hawkins |
| 5,902,723 A | 5/1999 | Dower et al. |
| 5,936,324 A | 8/1999 | Montagu |
| 5,952,170 A | 9/1999 | Stroun et al. |
| 5,981,956 A | 11/1999 | Stern |
| 6,025,601 A | 2/2000 | Trulson et al. |
| 6,027,889 A | 2/2000 | Barany et al. |
| 6,045,996 A | 4/2000 | Cronin et al. |
| 6,054,564 A | 4/2000 | Barany et al. |
| 6,063,603 A | 5/2000 | Davey et al. |
| 6,090,555 A | 7/2000 | Fiekowsky et al. |
| 6,141,096 A | 10/2000 | Stern et al. |
| 6,156,504 A | 12/2000 | Gocke et al. |
| 6,185,030 B1 | 2/2001 | Overbeck |
| 6,201,639 B1 | 3/2001 | Overbeck |
| 6,210,891 B1 | 4/2001 | Nyren et al. |
| 6,218,803 B1 | 4/2001 | Montagu et al. |
| 6,225,625 B1 | 5/2001 | Pirrung et al. |
| 6,258,540 B1 | 7/2001 | Lo et al. |
| 6,268,148 B1 | 7/2001 | Barany et al. |
| 6,309,824 B1 | 10/2001 | Drmanac |
| 6,310,199 B1 | 10/2001 | Smith et al. |
| 6,312,892 B1 | 11/2001 | Barany et al. |
| 6,316,229 B1 | 11/2001 | Lizardi |
| 6,329,179 B1 | 12/2001 | Kopreski |
| 6,342,387 B1 | 1/2002 | Hayashizaki et al. |
| 6,386,749 B1 | 5/2002 | Watts et al. |
| 6,391,623 B1 | 5/2002 | Besemer et al. |
| 6,401,267 B1 | 6/2002 | Drmanac |
| 6,410,276 B1 | 6/2002 | Burg et al. |
| 6,506,594 B1 | 1/2003 | Barany et al. |
| 6,534,262 B1 | 3/2003 | McKernan et al. |
| 6,534,293 B1 | 3/2003 | Barany et al. |
| 6,562,573 B2 | 5/2003 | Halaka |
| 6,573,103 B1 | 6/2003 | Wald |

(Continued)

FOREIGN PATENT DOCUMENTS

| | | |
|---|---|---|
| GB | 2299166 | 9/1996 |
| GB | 970444 | 3/1997 |

(Continued)

OTHER PUBLICATIONS

Enders, et al., "Fetal morbidity and mortality after acute human parvovirus B19 infection in pregnancy: prospective evaluation of 1018 cases", Prenatal Diagnosis, 24:513-18 (2004).

Smith, et al., "Quantitative phenotyping via deep barcode sequencing", Genome Res., 19:1836-42 (2009).

Van Opstal, et al. "Rapdi aneuploidy detection with multiplex ligation-dependent probe amplification: a prospective study of 4000 amniotice fluid samples", Eur. J. of Hum. Genetics, 17:112-21 (2009).

(Continued)

*Primary Examiner* — Jason Sims
(74) *Attorney, Agent, or Firm* — Convergent Law Group LLP

(57) ABSTRACT

The present invention provides processes for determining more accurate risk probabilities for medical conditions. The risk probabilities of the presence or absence of a medical condition are calculated using frequency data from selected biomolecules and biomolecule source contribution of at least one source in a mixed sample.

11 Claims, 8 Drawing Sheets

(56) References Cited

U.S. PATENT DOCUMENTS

| | | |
|---|---|---|
| 6,576,453 B2 | 6/2003 | Barany et al. |
| 6,797,470 B2 | 9/2004 | Barany et al. |
| 6,828,100 B1 | 12/2004 | Ronghi |
| 6,833,246 B2 | 12/2004 | Balasubramanian |
| 6,852,487 B1 | 2/2005 | Barany et al. |
| 6,858,412 B2 | 2/2005 | Willis et al. |
| 6,864,052 B1 | 3/2005 | Drmanac et al. |
| 6,911,345 B2 | 6/2005 | Quake et al. |
| 6,914,137 B2 | 7/2005 | Baker |
| 6,927,028 B2 | 8/2005 | Lo et al. |
| 6,949,370 B1 | 9/2005 | Barany et al. |
| 6,977,162 B2 | 12/2005 | Dhallan |
| 7,014,994 B1 | 3/2006 | Barany et al. |
| 7,083,917 B2 | 8/2006 | Barany et al. |
| 7,097,980 B2 | 8/2006 | Barany et al. |
| 7,166,434 B2 | 1/2007 | Barany et al. |
| 7,198,894 B2 | 4/2007 | Barany et al. |
| 7,208,274 B2 | 4/2007 | Dhallan |
| 7,232,656 B2 | 6/2007 | Balasubramanian et al. |
| 7,244,233 B2 | 7/2007 | Krantz et al. |
| 7,244,831 B2 | 7/2007 | Barany et al. |
| 7,312,039 B2 | 12/2007 | Barany et al. |
| 7,315,787 B2 | 1/2008 | Orlandi et al. |
| 7,320,865 B2 | 1/2008 | Barany et al. |
| 7,332,277 B2 | 2/2008 | Dhallan |
| 7,332,285 B2 | 2/2008 | Barany et al. |
| 7,343,190 B2 | 3/2008 | Krantz et al. |
| 7,358,048 B2 | 4/2008 | Barany et al. |
| 7,364,858 B2 | 4/2008 | Barany et al. |
| 7,429,453 B2 | 9/2008 | Barany et al. |
| 7,442,506 B2 | 10/2008 | Dhallan |
| 7,455,965 B2 | 11/2008 | Barany et al. |
| 7,459,311 B2 | 12/2008 | Nyren et al. |
| 7,527,929 B2 | 5/2009 | McKernan et al. |
| 7,556,924 B2 | 7/2009 | Barany et al. |
| 7,582,420 B2 | 9/2009 | Oliphant et al. |
| 7,598,060 B2 | 10/2009 | Dhallan |
| 7,601,491 B2 | 10/2009 | Collis et al. |
| 7,622,281 B2 | 11/2009 | Ronaghi et al. |
| 7,645,576 B2 | 1/2010 | Lo et al. |
| 7,648,824 B2 | 1/2010 | Nyren et al. |
| 7,700,323 B2 | 4/2010 | Willis et al. |
| 7,709,194 B2 | 5/2010 | Lo et al. |
| 7,709,201 B2 | 5/2010 | Barany et al. |
| 7,718,367 B2 | 5/2010 | Lo et al. |
| 7,718,370 B2 | 5/2010 | Dhallan |
| 7,727,720 B2 | 6/2010 | Dhallan |
| 7,727,727 B2 | 6/2010 | Collis |
| 7,754,428 B2 | 7/2010 | Lo et al. |
| 7,780,600 B2 | 8/2010 | Krantz et al. |
| 7,799,531 B2 | 9/2010 | Mitchell et al. |
| 7,807,431 B2 | 10/2010 | Barany et al. |
| 7,888,017 B2 | 2/2011 | Quake et al. |
| 7,901,884 B2 | 3/2011 | Lo et al. |
| 7,989,614 B2 | 8/2011 | Deggerdal et al. |
| 8,008,018 B2 | 8/2011 | Quake et al. |
| 8,195,415 B2 | 6/2012 | Fan et al. |
| 8,293,076 B2 | 10/2012 | Fan et al. |
| 2002/0045176 A1 | 4/2002 | Lo et al. |
| 2002/0132241 A1 | 9/2002 | Fan et al. |
| 2003/0003459 A1 | 1/2003 | Stahl |
| 2003/0044388 A1 | 3/2003 | Lo et al. |
| 2003/0054386 A1 | 3/2003 | Antonarakis et al. |
| 2003/0064366 A1 | 4/2003 | Hardin et al. |
| 2003/0108913 A1 | 6/2003 | Schouten |
| 2003/0143599 A1 | 7/2003 | Makarov et al. |
| 2004/0009518 A1 | 1/2004 | Lo et al. |
| 2004/0101835 A1 | 5/2004 | Willis et al. |
| 2004/0203037 A1 | 10/2004 | Lo et al. |
| 2004/0214175 A9 | 10/2004 | McKernan et al. |
| 2005/0095618 A1 | 5/2005 | Tsui et al. |
| 2005/0191656 A1 | 9/2005 | Drmanac et al. |
| 2006/0252068 A1 | 11/2006 | Lo et al. |
| 2006/0252071 A1 | 11/2006 | Lo et al. |
| 2006/0275789 A1 | 12/2006 | Willis et al. |
| 2007/0087345 A1 | 4/2007 | Olson-Munoz et al. |
| 2007/0207482 A1 | 9/2007 | Church et al. |
| 2007/0275402 A1 | 11/2007 | Lo et al. |
| 2008/0020390 A1 | 1/2008 | Mitchell et al. |
| 2008/0081338 A1 | 4/2008 | Lo et al. |
| 2008/0096766 A1 | 4/2008 | Lee |
| 2008/0206749 A1 | 8/2008 | Lo et al. |
| 2009/0018024 A1 | 1/2009 | Church et al. |
| 2009/0029377 A1 | 1/2009 | Lo et al. |
| 2009/0048124 A1 | 2/2009 | Leamon et al. |
| 2009/0061425 A1 | 3/2009 | Lo et al. |
| 2009/0087847 A1 | 4/2009 | Lo et al. |
| 2009/0155776 A1 | 6/2009 | Lo et al. |
| 2010/0105049 A1 | 4/2010 | Ehrich et al. |
| 2010/0105052 A1 | 4/2010 | Drmanac et al. |
| 2010/0112575 A1 | 5/2010 | Fan et al. |
| 2010/0112590 A1 | 5/2010 | Lo et al. |
| 2010/0120076 A1 | 5/2010 | Braun et al. |
| 2010/0136529 A1 | 6/2010 | Shoemaker et al. |
| 2010/0184043 A1 | 7/2010 | Mitchell et al. |
| 2010/0184044 A1 | 7/2010 | Mitchell et al. |
| 2010/0184210 A1 | 7/2010 | Rossmanith et al. |
| 2010/0267034 A1 | 10/2010 | Lo et al. |
| 2010/0291571 A1 | 11/2010 | Stoughton et al. |
| 2010/0291572 A1 | 11/2010 | Stoughton et al. |
| 2011/0003293 A1 | 1/2011 | Stoughton et al. |
| 2011/0027771 A1 | 2/2011 | Deng |
| 2011/0039724 A1 | 2/2011 | Lo et al. |
| 2011/0059451 A1 | 3/2011 | Mitchell et al. |
| 2011/0086357 A1 | 4/2011 | Lo et al. |
| 2011/0105353 A1* | 5/2011 | Lo et al. ............... 506/9 |
| 2011/0117548 A1 | 5/2011 | Mitchell et al. |
| 2011/0124518 A1 | 5/2011 | Cantor |
| 2011/0143342 A1 | 6/2011 | Lo et al. |
| 2011/0151442 A1 | 6/2011 | Fan et al. |
| 2011/0171638 A1 | 7/2011 | Stoughton et al. |
| 2011/0172111 A1 | 7/2011 | Cantor |
| 2011/0177517 A1 | 7/2011 | Rava et al. |
| 2011/0178719 A1 | 7/2011 | Rabinowitz |
| 2011/0183330 A1 | 7/2011 | Lo et al. |
| 2011/0201507 A1 | 8/2011 | Rava et al. |
| 2011/0224087 A1 | 9/2011 | Quake et al. |
| 2011/0230358 A1 | 9/2011 | Rava et al. |
| 2011/0245085 A1 | 10/2011 | Rava et al. |
| 2011/0276277 A1 | 11/2011 | Lo et al. |
| 2011/0288780 A1 | 11/2011 | Rabinowitz |
| 2011/0312503 A1 | 12/2011 | Chuu |
| 2012/0003650 A1 | 1/2012 | Lo et al. |
| 2012/0010085 A1 | 1/2012 | Rava |
| 2012/0100548 A1 | 4/2012 | Rava et al. |
| 2012/0108460 A1 | 5/2012 | Quake et al. |
| 2012/0165203 A1 | 6/2012 | Quake et al. |
| 2012/0225798 A1 | 9/2012 | Cantor et al. |
| 2012/0237928 A1 | 9/2012 | Rava et al. |
| 2012/0264115 A1 | 10/2012 | Rava |
| 2012/0264121 A1 | 10/2012 | Rava et al. |
| 2012/0270739 A1 | 10/2012 | Rava et al. |

FOREIGN PATENT DOCUMENTS

| | | |
|---|---|---|
| WO | WO87/06270 | 10/1987 |
| WO | WO90/06995 | 6/1990 |
| WO | WO99/47964 | 9/1999 |
| WO | WO03/038120 | 5/2003 |
| WO | WO2007/100243 | 9/2007 |
| WO | WO2007/126377 | 11/2007 |
| WO | WO2008/118998 | 10/2008 |
| WO | WO2009/036525 | 3/2009 |
| WO | WO2009/102632 | 8/2009 |
| WO | WO2011/090556 | 1/2010 |
| WO | WO2011/090557 | 1/2010 |
| WO | WO2011/090558 | 1/2010 |

OTHER PUBLICATIONS

Xie and Tammi, "CNV-seq, a new method to detect copy number variation using high throughput sequencing", BMC Bioinformatics, 10:80 (2008), doi 10.1186/1471-2105-10-80, p. 1-9.

Office Action for U.S. Appl. No. 13/356,133 (inventor A. Oliphant, filed Jan. 23, 2012), entire document.

(56) References Cited

OTHER PUBLICATIONS

Office Action for U.S. Appl. No. 13/356,575 (inventor A. Oliphant, filed Jan. 23, 2012), entire document.
Office Action for U.S. Appl. No. 13/689,206 (inventor A. Oliphant, filed 39 Nov. 2012).
Final Office Action for U.S. Appl. No. 13/689,206 (inventor A. Oliphant, filed 39 Nov. 2012), entire document.
Office Action for U.S. Appl. No. 13/013,732 (inventor A. Oliphant, filed Jun. 25, 2011).
Office Action for U.S. Appl. No. 13/013,732 (inventor A. Oliphant, filed Jun. 25, 2011), entire document.
Office Action for U.S. Appl. No. 13/407,978 (inventor K. Song, filed Feb. 29, 2012), entire document.
Office Action for U.S. Appl. No. 13/205,490 (inventor A. Sparks, filed Aug. 8, 2011), entire document.
Office Action for U.S. Appl. No. 13/687,169 (inventor A. Sparks, filed Nov. 28, 2012), entire document.
Office Action for U.S. Appl. No. 13/205,570 (inventor A. Sparks, filed Aug. 8, 2011), entire document.
Office Action for U.S. Appl. No. 13/687,025 (inventor A. Sparks, filed Nov. 28, 2012), entire document.
Office Action for U.S. Appl. No. 13/293,419 (inventor A. Sparks, filed Nov. 10, 2011), entire document.
Final Office Action for U.S. Appl. No. 13/293,419 (inventor A. Sparks, filed Nov. 10, 2011), entire document.
Advisory Action for U.S. Appl. No. 13/293,419 (inventor A. Sparks, filed Nov. 10, 2011), entire document.
Office Action for U.S. Appl. No. 13/245,133 (inventor A. Oliphant, filed Sep. 26, 2011), entire document.
Office Action for U.S. Appl. No. 13/316,154 (inventor A. Oliphant, filed Dec. 9, 2011), entire document.
Office Action for U.S. Appl. No. 13/338,963 (inventor A. Oliphant, filed Dec. 28, 2011), entire document.
Office Action for U.S. Appl. No. 13/689,417 (inventor A. Oliphant, filed Nov. 29, 2012), entire document.
Search Report (PCT/US2011/046963), entire document.
Search Report (PCT/US2012/70177), entire document.
Cirigiliano, et al., "Clinical application of multiplex quantitative fluorescent polymerase chain reaction QF-PCR for the repaid prenatal detection of common chromosome aneuploidies", Molecular Human Reproduction, 7(10):1001-06 (2001).
Cirigiliano, et al., "Rapid prenatal diagnosis of common chromosome aneuploidies by QF-PCR, results of 9 years of clinical experience", Prenatal diagnosis, 29:40-49 (2009).
Choo, et al., "A homologous subfamily of satellite III DNA on human chromosomes 14 and 22", Nucleic Acids Research, 18(19):5641-47 (1990).
Choo, et al., "A Chromosome 14-specific Human Satellite III DNA Subfamily That Shows Variable Presence on Different Chromosomes 14", Am J. Hum. Genet., 50:706-16 (1992).
Chromosome 14 map.
Chu, et al., "A novel approach toward the challenge of accurately quantifying fetal DNA in maternal plasma", Prenat. Diag., 30:1226-29 (2010).
Ciccodicola, et al., "Differentially regulated and evolved genes in the fully sequences Xq/Yq pseudoautosomal region", Hum. Mol. Genet., 9(3):395-401 (2000).
Cockwell, et al., "Distribution of the D15A1 copy number polymorphism", European J. of Hum. Genet., 15:441-45 (2007).
Conover, Practical Nonparametric Statistics, pp. 295-01 (John Wiley & Sons, NY)(1971).
Costa, et al., "New strategy for prenatal diagnosis of X-linked disorders", N. Engl J. Med., 346:1502 (2002).
Stroun, et al., "Neoplastic Characteristics of the DNA Found in the Plasma of Cancer Patients", Oncology, 46: 318-322 (1989).
Stroun, et al., "Isolation and Characterization of DNA from the Plasma of Cancer Patients", Eur. J. Cancer Clin. Oncol., 23(6)707-12 (1987).

Sullivan, et al., "Evidence for Structural Heterogeneity from Molecular Cytogenetic Analysis of Dicentric Robertsonian Translocations", Am. J. Hum. Genet., 59:167-75 (1996).
Tong, et al., "Noninvasive prenatal detection of fetal trisomy 18 by epigenetic allelic ratio analysis in maternal plasma: theoretical and empirical considerations", Clin Chem, 52:2194-202 (2006).
Tsui, et al., "Systematic microarray-based identification of placental mRNA in maternal plasma: towards non-invasive prenatal gene expression profiling", J. Med Genet, 41:461-67 (2004).
Tsui, et al., "Noninvasive prenatal diagnosis of hemophilia by microfluidics digital PCR analysis of maternal plasma DNA", Blood, 117:3684=91 (2011).
Vogelstein, et al., "Digital PCR", PNAS USA, 96:9236-41 (1999).
Wachtel, et al., "Fetal cells in the maternal circulation: Isolation by multiparameter flow cytometry and confirmation by polymerase chain reaction", Human Reprod., 6(10):1466-69 (1991).
Wald, et al., "Maternal serum screening for Down's syndrome in early pregnancy", BMJ, 297:883-87 (1988).
Wald, et al., "Antenatal maternal serum screening for Down's syndrome: results of a demonstration project", BMJ, 305(6850):391-94 (1992).
Wang, et al., "PennCNV: An integrated hidden Markov model designed for high-resolution copy number variation detection in whole-genome SNP genotyping data", Genome Res., 17:1665-74 (2007).
Ward, et al. "Reactivities of serotyping monoclonal antibodies with culture-adapted human rotaviruses", J. Clin. Microbiol. 29(3):422-25 (1991).
Winsor, et al., "Maternal Cell Contamination in Uncultured Amniotic Fluid", Prenatal Diagnosis, 16:49-54 (1996).
Wu and Wallace, "The ligation amplification reaction (LAR)—Amplification of specific DNA sequences using sequential rounds of template-dependent ligation", Genomics, 4:560-69 (1989).
Young and Davis, "Efficient isolation of genes by using antibody probes", PNAS 80:1194-98 (1983).
Lapair, et al., "Cell-Free DNA in Amniotic Fluid: Unique Fragmentation Signatures in Euploid and Aneuploid Fetuses", Clinical Chem., 53(3):405-11 (2007).
Office Action for U.S. Appl. No. 13/293,419.
Search Report for (PCT/US2012/21955).
Search Report for PCT/US2011/046935).
Search Report for (PCT/US2012/026754).
Heilig, et al., "The DNA sequence and analysis of human chromosome 14", Nature, 421:601-09 (2003).
Hosny, et al., "TP53 mutations in circulating fee DNA from Egyptian patients with non-Hodgkin's lymphoma", Cancer Lett., 275(2):234-39 (2009).
Irizarry, et al., "Summaries of Affymetrix GeneChip probe level data", Nuc. Acid Res., 31(4):e5 (2003).
Kamnasaran and Cox, "Current status of chromosome 14", J. Med. Genet., 39:81-90 (2002).
Landegren, et al., "A ligase-mediated gene detection technique", Science, 241:1077 (1988).
Leon, "Free DNA in the Serum of Cancer Patients and the Effect of Therapy", Cancer Res., 37:646-50 (1977).
Li, et al., "A photocleavable fluorescent nucleotide for DNA sequencing and analysis", PNAS USA, 100(2):414-19 (2003).
Liao, et al. "Targeted massively parallel sequencing of maternal plasma DNA permits efficient and unbiased detection of fetal alleles", Clin Che, 57:92-101 (2011).
Lo, et al., "Detection of single-copy fetal DNA sequence from maternal blood", The Lancet, 335:1463-64 (1990).
Lo, et al., "Two-way cell traffic between mother and fetus: biological and clinical implications", Blood, 88:4390-95 (1996).
Lo, et al., "Presence of fetal DNA in maternal plasma and serum", The Lancet, 350:485-86 (1997).
Lo, et al., "Quantitative analysis of fetal DNA in maternal plasma and serum: implications for noninvasive prenatal diagnosis", Am J. Hum. Genetics, 62:768-75 (1998).
Lo, et al., "Prenatal diagnosis of fetal RhD status by molecular analysis of maternal plasma", N Engl J Med, 339:1734-38 (1998).
Lo, et al., "Rapid clearance of fetal DNA from maternal plasma", Am J. Hum. Genetics, 64:218-24 (1999).

(56) References Cited

OTHER PUBLICATIONS

Lo, et al., "Digital PCR for the molecular detection of fetal chromosomal aneuploidy", PNAS USA, 104:13116-21 (2007).
Lo, et al., "Plasma placental RNA allelic ratio permits noninvasive prenatal chromosomal aneuploidy detection", Nat. Med., 13:218-23 (2007).
Lo, et al., Maternal plasma DNA sequencing reveals the genome-wide genetic and mutational profile of the fetus. Sci Transl Med, 2:61ra91 (2010).
Lo, "Fetal nucleic acids in maternal blood: the promises", Clin. Chem. Lab Med., 50(5):xxx-xxx (DOI 10.1515/CCLM.2011.765) (2011).
Lun, et al., "Microfluidics Digital PCR Reveals a Higher than Expected Fraction of Fetal DNA in Maternal Plasma", Clin. Chem., 54(10):1664-72 (2008).
Lun, et al., "Noninvasive prenatal diagnosis of monogenic diseases by digital size selection and relative mutation dosage on DNA in maternal plasma", PNAS USA, 105(50):19920-25 (2008).
Makrigiorgos, et al., "A PCR-based amplification method retaining the quantitative difference between two complex genomes", Nat. Biotech., 20:936-39 (2002).
Mangs, Curr. Genomics, "The Human Pseudoautosomal Region (PAR): Origin, Function and Future", 8(2):129-36 (2007).
Mansfield, "Diagnosis of Down syndrome and other aneuploidies using quantitative polymerase chain reaction and small tandem repeat polymorphisms", Human Molecular Genetics, 2(1):43-50 (1993).
Mantzaris, et al., "Preliminary report: correct diagnosis of sex in fetal cells isolated from cervical mucus during early pregnancy", ANZJOG, 45(6):529-32 (2005).
Mujezinovic and Alfirevic, Obstet. Gynecol., "Procedure-Related Complications of Amniocentesis and Chorionic Villous Sampling: A Systematic Review", 110(3):687-94 (2007).
Mueller, et al., "Isolation of fetal trophoblast cells from peripheral blood of pregnant women", The Lancet, 336:197-200 (1990).
Nawroz, et al., "Microsatellite alterations in serum DNA of head and neck cancer patients", Nature Medicine, 2(9):1035-37 (1996).
Ng, et al., "mRNA of placental origin is readily detectable in maternal plasma", PNAS USA, 100:4748-53 (2003).
Page, et al., "Breakpoint diversity illustrates distinct mechanisms for Robertsonian translocation formation", Hum. Molec. Genet., 5(9):1279-88 (1996).
Page, et al., Br. J. Cancer, "Detection of HER2 amplification in circulating free DNA in patients with breast cancer", 104(8):1342-48 (2011).
Papageorgiou, et al., "DNA methylation ratio permits noninvasive prenatal diagnosis of trisomy 21", Nat. Med., 17:510-13 (2011).
Petersen, et al., "Down Syndrome Due to De Novo Robertsonian Translocation t(14q21q): DNA Polymorphism Analysis Suggests that the Origin of the Extra q21 is Maternal", Am. JU. Hum. Genet. 49:529-36 (1991).
Poon, et al., "Differential DNA methylation between fetus and mother as a strategy for detecting fetal DNA in maternal plasma", Clin Chem, 48:35-41 (2002).
Rijinders, et al., "Fetal sex determination from maternal plasma in pregnancies at risk for congenital adrenal hyperplasia", Obstet Gynecol, 98:374-78 (2001).
Ro, et al., "Association of Polymorphisms of Interleukin-8, CXCR1, CXCR2, and Selectin With Allograft Outcomes in Kidney Transplantation", Transplantation, 91(1):57-64 (2011).
Ross, et al., "The DNA sequence of the human X Chromosome", Nature 434:325-37 (2005).
Roth, et al., Molec. Oncol., "Screening for circulating nucleic acids and caspase activity in the peripheral blood as potential diagnostic tools in lung cancer", 5(3):281-91 (2011).
Royston, "An extension of Shapiro and Wilk's W test for normality to large samples", Applied Statistics, 31:115-24 (1982).
Royston, "Model-based screening by risk with application to Down's syndrome", Statistics in Medicine, 11(2)257-68 (1992).
St. Clair, "Copy Number Variation and Schizophrenia", Schizophr. Bull., 35(1):9-12 (2009).
Savas, "Useful genetic variation databases for oncologists investigating the genetic basis of variable treatment response and survival in cancer", Acta Oncol., 49(8):1217-26 (2010).
Schuster, et al, "Next-generation sequencing transforms today's biology", Nat. Methods, 5:16-18 (2008).
Scriven, et al., "Robertsonian translocations—reproductive reisks and indications for preimplantation genetic diagnosis", Human Reproduction, 16(11):2267-73 (2001).
Sebat, et al., "Strong Association of De Novo Copy Number Mutations with Autism", Science, 316(5823):445-49 (2007).
Sehnert, et al., "Optimal detection of fetal chromosomal abnormalities by massively parallel DNA sequencing of cell-free fetal DNA from maternal blood", Clin Chem, 57: 1042-49 (2011).
Shamash, et al., "Preimplantation genetic haplotyping a new application for diagnosis of translocation carrier's embryo—preliminary observations of two robertsonian translocation carrier families", J. Assist. Reprod. Genet., 28:77-83 (2011).
Simpson and Elias, "Isolating Fetal Cells from Maternal Blood", JAMA, 270(19):2357-61 (1993).
Simpson, "Is Cell-Free Fetal DNA from Maternal Blood Finally Ready for Prime Time?", Obst & Gynecol., 119(5):1-3 (2012).
Snyder, et al., "Universal noninvasive detection of solid organ transplant rejection", PNAS USA, 108(5):6229-34 (2011).
Sorenson, "Cancer Epidemiology, Biomarkers and Prevention", Cancer Epidem. Biomarkers Prev., 3_67-71 (1994).
Search Report for (PCT/US2012/022261).
Ashoor, et al., "Chromosome-selective sequencing of maternal plasma cell-free DNA for first-trimester detection of trisomy 21 and trisomy 18", Am. J. of Obstet. Gynecol., (2012), doi: 10.1016/j.ajog.2012.01.029.
Bodurtha and Strauss, "Genomics and Prenatal Care", New Eng. J. of Medicine, 366:64-73 (2012).
Chiu, et al., "Noninvasive prenatal diagnosis of fetal chromosomal aneuploidy by massively parallel genomic sequencing of DNA in maternal plasma", PNAS USA 105:20458-63 (2008) Supporting Information.
Sparks, et al., "Noninvasive prenatal detection and selective analysis of cell-free DNA obtained from maternal blood: evaluation for trisomy 21 and trisomy 18", Am. J. Obstet. Gynecol., (2012), 206:319.e1-9.
Sparks, et al., "Selective analysis of cell-free DNA in maternal blood for evaluation of fetal trisomy", Prenatal Diagnosis, 32:1-7 (2012).
Sparks, et al., "Non-invasive Prenatal Detection and Selective Analysis of Cell-free DNA Obtained from Maternal Blood: Evaluation for Trisomy 21 and Trisomy 18", Am. J. Obstet. Gynecol., (2012), doi:10.1016/j.ajog.2012.01.030.
Search Report for (PCT/US2011/046976).
Office Action for U.S. Appl. No. 13/013,732.
International Search Report for PCT/US2011/046981, dated Oct. 15, 2012.
Final Office Action dated Dec. 7, 2012 on U.S. Appl. No. 13/013,732.
Final Office Action dated Oct. 12, 2012 on U.S. Appl. No. 13/013,732.
Tomilin, et al., "Mechanisms of Chromosome Destabilization in Human Cells", Sov. Sci. Rev. D. Physiochem. Biol., 10:39-89 (1992).
Ulbright, "Germ cell tumors of the gonads: a selective review emphasizing problems in differential diagnosis, newly appreciated, and controversial issues," Modern Pathology, 18:S61-S79 (2005).
Vasioukhin, et al., "Point mutations in the N-ras gene in the blood plasma DNA of patients with myelodysplastic cyndrome or acute myelogenous leukaemia", British J. of Haematology, 86:774-79 (1994).
Walker, et al., "Human DNA quantitation using Alu element-based polymerase chain reaction", Analytical Biochem., 315:122-28 (2003).
Witt, et al., "An improved, non-isotopic method of screening cells from patients with abnormalities of sexual differentiation for Y chromosomal DNA content", J. Med. Genet., 30:304-07 (1993).
Abadia-Molina, et al., "Immune phenotype and cytotoxic activity of lymploycytes from human term decidua against trophoblast", J. of Reproductive Immunology, n31:109-23 (1996).

(56) References Cited

OTHER PUBLICATIONS

Anker, et al., "Spontaneous Release of DNA by Human Blood Lymphocytes as Shown in an in Vitro System", Cancer Research, 35:2375-82 (1975).
Anker, et al., "K-ras Mutations are found in DNA extreacted from the plasma of patients with colorectal cancer," Gastroenterology, 112:1114-20 (1997).
Anker, et al., Information carried by the DNA release by antigen-stimulated lymphocytes:, Immunology, 37:753-63 (1979).
Ashoor, et al., Fetal Fraction in Maternal Plasma Cell-Free DNA at 11-13 Weeks' Gestation: Effect of Maternal and Fetal Factors, Fetal Dian Ther DOI:10.1159/000337373 (Pub'd online May 4, 2012).
Batzer and Deininger, "ALU Repeats and Human Genomic Diversity", Nature, 3:370-79 (2002).
Beard, "Embryological Aspects and Etiology of Carcinoma", The Lancet, Jun. 21, 1902, pp. 1758-1761.
Belokhvostov, et al. "Changes in the Fractional Composition of the Nucleic Acids in Blood Serum upon Rediation Damage Early Stage Abnormalities Following Gamma-Irradiation of Rats", Tsitologiia (Cytology) 1986.
Bradstock, et al., "Functional and phenotypic assessment of neonatal human leucocytes expressing natural killer cell-associated antigen", Immunology and Cell Biology (71:535-42 (1993).
Campbell, et al., "Subclonal phylogenetic structions in cancer revealed by ultra-deep sequencing", PNAS, 105(35):13081-86 (2008).
Cicuttini and Boyd, "Hemopoietic and Lymphoid Progenitro Cells in Human Umbilical Cord Blood", Developmental Immunology, 4:1-11 (1994).
Datta, et al., "Sensitive Detection of Occult Breast Cancer by the Reverse-Transcriptase Polymerase Chain Reaction", J. of Clinical Oncology, 12(3): 475-82 (1994).
Dennin, "DNA of Free and Complexed Origin in Human Plasma: Concentration and Length Distribution", Klin. Wochenschr., 57:451-56 (1979).
Fisher, et al., "Genetic evidence that placental site trophoblastic tumours can originate from a hydatidiform mole or a normal conceptus", Br. J. Cancer, 65:355-358 (1992).
Fournie, et al., "Plasma DNA as Cell Death Marker in Elderly Patients", Gerontology, 39:215-221 (1993).
Geifman-Holzman, et al., "Fetal RhD genotyping in fetal cells flow sorted from maternal blood", Am. J. Obstet. Gynecol., 174(3):818-22 (1996).
Ghossein, et al.. "Detection of Circulating Tumor Cells in Patients With Localized and Metastatic Prostatic Carcinoma Clinical Implications", J. of Clin. Oncology, 13(5):1995-200 (1995).
Green, et al., "Gestational Trophoblastic Disease: A Spectrum of Radiologic Diagnosis", Radiographics, 16(6):1371-84 (1996).
Gribben, et al., "Detection of Residual Lymphoma Cells by Polymerase Chain Reaction in Peripheral Blood is Significantly Less Predictive for Relapse Than Detection in Bone Marrow", Blood, 83(12):3800-07 (1994).
Hardingham, et al., "Detection of Circulating Tumor Cells in Colorectal Cancer by Immunogead-PCR is a Sensitive Prognostic marker for Relapse of Disease", Molecular Medicine, 1(7):789-94 (1995).
Heid, et al., "Real Time Quantitative PCR", Genome Res., 6:986-94 (1996).
Ho, et al., "Activation Status of T and NK Cells in the Endometrium Throughout Menstrual Cycle and Normal and Abnormal Early Pregnancy", Human Immunology, 49:130-36 (1996).
Hoon, et al., "Detection of Occult Melanoma Cells in Blood With a Multiple-Marker Polymerase Chain Reaction Assay", J. of Clinical Oncology, 13(8):2109-116 (1995).
International Human Genome Sequencing Consortium, "Initial sequencing and analysis of the human genome", Nature, 409:860-921 (2001).
Kazakov, et al., "Extracellular DNA in the Blood of Pregnant Women", Tsitologiia (Cytology), 37(3):232-37 (1995).
Kogan, et al., "An improved method for prenatal diagnosis of genetic diseases by analysis of amplified DNA sequences", New England J. of Medicine, 317(6):985-90 (1987).
Krebs, et al., "The Unitarian or Trophoblastic Thesis of Cancer" Medical Record, 163:149-74 (Jul. 1950).
Margulies, et al., "Genome sequencing in microfabricated high-density picolitre reactors", Nature, 437(15):376-80 and errata (2005), 1989.
Mikhaylov, et al., "Changes in the quantity and synthesis of DNA in the nuclei of large decidual cells of rats in the course of their differentiation", Tsitologiia (Cytology),41(6):677-83.
Mikhaylov, et al., "Synthesis and content of DNA in human decidual cells at various stages of differentiation according to flow cytometry analysis", Tsitologiia (Cytology), 34(6):67-72 (1992).
Moffet-King, et al., "Natural Killer Cells and Pregnancy", Nature Reviews Immunology, 2002(2):656-63.
Moreno and Gomella, "Circulating Prostate Cancer Cells Detected by Reverse Transcription-Polymerase Chain Reaction (RT-PCR: What do they mean?", Cancer Control Journal, 5(6), 1998.
Mulcahy, et al., "Plasma DNA K-rase Mutations in Patients with Gastrointestinal Malignancies," Annals New York Academy of Sciences, 25-28, 1999.
Nelson, et al., "Alu polymerase chain reaction: A method for rapid isolation of human-specific sequence from complex DNA sources," PNAS USA, 86:6686-90 (1989).
Paolella, et al., "The Alu family repeat promoter has a tRNA-like bipartite structure", EMBO J., 2(5):691-96 (1983).
Oei, et al., "Clusters of regulatory signals for RNA polymerase II transcription associated with Alu family repeats and CpG islands in human promoters", Genomics, 83:873-82 (2004).
Robbins, et al., *Pathologic Basis of Disease 5th Ed.*, Chapter 23, pp. 1071-1088 (1994).
Ronaghi, et al., "A Sequencing Method Based on Real_Time Pyrophosphate", Science, 281:363-65 (1998).
Saiki, et al., "Primer-directed Enzymatic Amplification of DNA with a Thermostable DNA Polymerase", Science, 239:487-91 (1987).
Schallhammer, et al., "Phenotypic comparison of natural killer cells from peripheral blood and from early pregnancy decidua", Early Pregnancy: Biology and Medicine, 3:15-22 (1997).
Schroder, et al., "Transplacental passage of blood cells", J. of Medical Genetics, 12:230-42 (1974).
Shapiro, et al., "Determination of Circulating DNA Levels in Patients with Benign or Malignant Gastrointestinal Disease", Cancer, 51:2116-20 (1983).
Shendure, et al., "Accurate Multiplex Polony Sequencing of an Evolved Bacterial Genome", Science, 309:1728-32 (2005).
Simpson, et al., "Isolating Fetal Cells in Maternal Circulation for Prenatal Diagnosis", Prenatal Diagnosis, 14:1229-42 (1994).
Smith, et al. "Detection of melanoma cells in peripheral blood by means of reverse transcriptase and polymerase chain reaction", The Lancet, 338:1227-29 (1991).
Smith, et al.. "Placental apoptosis in normal human pregnancy", Am. J. Obstet. Gynecol, Jul. 1997, pp. 57-65.
Sorenson, et al., "Soluble normal and mutated DNA sequences from single-copy genes in human blood", Cancer Epidemmiol. Biomarkers, 3:64-71 (1994).
Stroun, et al., "Circulating Nulceic Acids in Higher Organisms", Rev. Cytol. 51:1-48 (1977).
Stroun, et al., The Origin and Mechanism of Circulating DNA, Annals New York Academy of Sciences, 906:161-68 (2000).
Tagle, et al., "An optimized Alu-PCR primer pair for human-specific amplification of YACs and somatic cells hybrids", Human Molecular Genetics, 1(2):121-22 (1992).
Agostini, et al., "Circulating cell-free DNA: a promising marker of pathologic tumor response in rectal cancer patients receiving pre-operative chemotherapy", Ann. Surg. Oncol., 18(9):2461-68 (2011).
Alexandrov, et al., "Definition of a new alpha satellite suprachromosomal family characterized by monomeric organization", Nucleic Acids Research, 21(9):2209-15 (1003).
Arnheim, et al., "Molecular evidence for genetic exchanges among ribosomal genes on nonhomologous chromosomes in man and apes", PNAS USA, 77(12):7323-27 (1980).

(56) References Cited

OTHER PUBLICATIONS

Bandyopadhyay, et al, "Identification and characterization of satellite III subfamilies to the acrocentric chromosomes", Chromosome Research, 9:223-33 (2001).

Bianchi, "Prenatal diagnosis by analysis of fetal cells in maternal blood", J. of Pediatrics, 127(6):847-56 (1995).

Bianchi, "Isolation of fetal DNA from nucleated erythrocytes in maternal blood", PNAS USA, 87:3279-83 (1990).

Bianchi, "PCR Quantitation of Fetal Cells in Maternal Blood in Normal and Aneuploid Pregnancies", Am J. Hum. Genet., 61:822-29 (1997).

Biran, "On the Oncodevelopmental Rold of Human Imprinted Genes", 43:119-23 (1994).

Blaschke and Rappold, "The Pseudoautosomal regions, SHOX and disease", Curr. Opin. Gene. Dev., 16(3):23-29 (2006).

Bombard, et al., "Fetal RHD genotype detection from circulating cell-free DNA in maternal plasma in non-sensitized RhD negative women", Prenat Diagn, 31:802-08 (2011).

Camaschella, et al., "Prenatal Diagnosis of Fetal Hemoglobin Lepore-Boston Disease on Maternal Peripheral Blood", Blood, 75(11):2102-06 (1990).

Cappuzzo, et al., "Epidermal growth factor receptor gene and protein and gefitinib sensitivity in non-small-cell lung cancer", J. Natl Cancer Inst., 97(9):643-55 (2005).

Chen, et al., "Microsatellite alterations in plasma DNA of small cell lung cancer patients", Nature Medicine, 2(9):1033-35 (1996).

Chen, et al., "Noninvasive prenatal diagnosis of fetal trisomy 18 and trisomy 13 by maternal plasma DNA sequencing", PLos One, 6:e21791 (2011).

Chim, et al., "Detection of the placental epigenetic signature of the *maspin* gene in maternal plasma", PNAS USA, 102(41):14753-58 (2005).

Chiu, et al, "Effects of Blood-Processing Protocols on Fetal and Total DNA Quantification in Maternal Plasma", Clin. Chem., 47(9):1607-1613 (2001).

Chiu, et al., "Maternal plasma DNA analysis with massively parallel sequencing by ligation for noninvasive prenatal diagnosis of trisomy 21", 56:459-63 (2010).

Chiu, et al, "Noninvasive prenatal diagnosis of fetal chromosomal aneuploidy by massively parallel genomic sequencing of DNA in maternal plasma", PNAS USA 105:20458-63 (2008).

Chiu and Lo, "Non-invasive prenatal diagnosis by fetal nucleic acid analysis in maternal plasma: the coming of age", Semin. Fetal Neonatal Med., 16(2):88-93 (2011).

Chiu, et al., "Non-invasive prenatal assessment of trisomy 21 by multiplexed maternal plasma DNA sequencing: large scale validity study", Br Med J. 342:c7401 (2011).

Dear, et al., "A High-Resolution Metric Happy Map of Human Chromosome 14" Genmoics, 48 232-41 (1998).

Dhallan, et al., "A non-invasive test for prenatal diagnosis based on fetal DNA present in maternal blood: a preliminary study", Lancet, 369(9560):474-81 (2007).

Dobrzycka, et al., "Circulating free DNA and p53 antibodies in plasma of patients with ovarian epithelial cancers", Annals of Oncology, 22:1133-40 (2011).

Dobrzycka, et al., "Prognostic significance of VEGF and its receptors in endometrioid endometrial cancer", Ginekol Pol. 81(6):422-25 (2010).

Duan, et al., "PstSNP-HapMap3: a database of SNPs with high population differentiation for HapMap3", Bioinformation, 3(3):139-41 (2008).

Earle, et al., "Identification of DNA Sequences Flanking the Breakpoin of Human t(14q21q) Robertsonian Translocations", Am J. Hum Genet., 50:717-24 (1992).

Ehrich, et al., "Noninvasive detection of fetal trisomy 21 by sequencing of fetal DNA in maternal blood: a study in a clinical setting", AM J. Obstet Gynecol, 2011:204:205 e1-11 (2011).

Fan, et al., "Noninvasive diagnosis of fetal aneuploidy by shotgun sequencing DNA from maternal blood", PNAS USA, 105(42):16266-71 (2008).

Fan, et al., "Analysis of the Size Distributions of Fetal and Maternal Cell-Free DNA by Paired-End Sequencing", Clin. Chem., 56(8):1279-80 (2010).

Fan, et al., "Sensitivity of noninvasive prenatal detection of fetal aneuploidy from maternal plasma using shotgun sequencing is limited only by counting statistics", PLoS One, 5:e10439 (2010).

Fejgin, et al., "Fetal cells in the uterine cervix: a source for early non-invasive prenatal diagnosis", Prenat. Diag., 21:619-21 (2001).

Finning, et al., "Effect of high throughput RHD typing of fetal DNA in maternal plasma on use of anti-RhD immunoglobulin in RhD negative pregnant women: prospective feasibility study", Br Med J., 336:816-18 (2008).

Fisher, et al., "Genetic evidence that placental site trophoblastic tumours can originate from a hydatidiform mole or a normal conceptus", Br. J. Cancer, 65:355-58 (1992).

Fowke, Genetic analysis of human DNA recovered from minute amounts of serum and plasma, J. of Immunol. Meth., 180:45-51 (1995).

Gold, "Cancer and Pregnancy: Parallels in Growth, Invasion, and Immune Modulation and Implicationsa for Cancer Therapeutic Agents", Mayo Clin. Proc., 84(11):985-1000 (2009).

Gosden, et al., "Satellite DNA Sequences in the Human Acrocentric Chromosomes: Information from Translocations and Heteromorphisms", Am. J. Hum. Genet., 33:243-51 (1981).

Greeley, et al., "Get ready for the flood of fetal gene screening", Nature, 469:289-91 (2011).

Guatelli, et al., "Isothermal, in vitro amplification of nucleic acids by a multienzyme reaction modeled after retroviral replication", PNAS USA, 87(5):1874- (1990).

Han, et al, "Molecular Chytogenetic Characterization of 17 rob(13q14q) Robertsonian Translocations by Fish, Narrowing the Region Containing the Breakpoints", Am J. Hum. Genet., 55:960-67 (1994).

Harrell, Regression modeling strategies, §§9.2.2 and 1.10.5 (Springer Vertag)(2001).

* cited by examiner

ENHANCED RISK PROBABILITIES USING BIOMOLECULE ESTIMATIONS

CROSS-REFERENCE TO RELATED APPLICATIONS

The present application claims priority to U.S. Ser. No. 61/436,135, filed Jan. 25, 2011, which is herein incorporated by reference in its entirety.

FIELD OF THE INVENTION

This invention relates to quantification of biomolecule levels to calculate health risk probabilities in samples comprising biomolecules from two or more sources. (Note: For support for these amendments, please see the abstract.)

BACKGROUND OF THE INVENTION

In the following discussion certain articles and processes will be described for background and introductory purposes. Nothing contained herein is to be construed as an "admission" of prior art. Applicant expressly reserves the right to demonstrate, where appropriate, that the articles and processes referenced herein do not constitute prior art under the applicable statutory provisions.

The ability to detect the presence or absence of biomolecules in samples from a patient has enabled risk assessment for a variety of medical conditions, ranging from infectious disease to cancers to fetal abnormalities. The ability to determine more accurate risk assessments not only identifies the likelihood of various health conditions, in many cases it aids in informing decisions on potential therapeutic approaches and/or interventional techniques. However, in general non-invasive, conventional mechanisms for detecting biomolecules lack desired sensitivity and specificity and typically detect only one type of molecule at a time.

For example, biomolecules are detected in current prenatal screening tests to indicate a likelihood of fetal abnormalities, including Down Syndrome. AFP is a protein secreted by the fetal liver and excreted in the mother's blood, and a low level of AFP could also indicate Down Syndrome. The triple screen measures not only AFP, but beta-hCG and unconjugated estriol (uE3) as well, and the quadruple screen measures these three markers as well as inhibin A.

Although the use of additional markers increases the accuracy of the screening, even the combined biomolecule screening tests have issues. The detection rate for Down Syndrome is estimated to be 59% using the double test (AFP and hCG), 69% using the triple test (AFP, hCG, uE3), and 76% using the quadruple test (AFP, hCG, uE3, inhibin A), all in combination with maternal age. Wald N J et al., J Med Screen 1997 4:181-246. The tests used to confirm a positive screening result (e.g., amniocentesis or chorionic villus sampling) are invasive and carry up to a 1% rate of miscarriage of otherwise healthy, normal fetuses.

Enhanced methods to determine biomolecule levels associated with risk probabilities for various medical conditions are thus needed. (Note: For support for these amendments, please see the abstract.)

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present invention provides processes for calculating more accurate risk probabilities of the presence or absence of a medical condition associated with levels of biomolecules in a sample. Specifically, the invention provides processes for calculating risk probabilities to predict the presence or absence of a medical condition in a subject using 1) frequency data on selected biomolecules within a mixed sample from the subject and 2) biomolecule source contribution data from at least one biomolecule source in the mixed sample. Sources of biomolecules can be any different originating sources of the biomolecules from a subject.

In preferred aspects, the biomolecules are nucleic acids from host cells and non-host cells present in the subject, e.g., nucleic acids from the subject and from fetal cells, infectious organisms, donor tissue, or cancerous cells and the like. In preferred aspects, the biomolecules are cell free nucleic acids present in a mixed sample, e.g., cell free DNA arising from host cells (e.g., the mother or transplant recipient) and source non-host (e.g., the fetus or transplant donor cells).

The mixed sample used in the processes of the invention can be any sample from an individual which comprises biomolecules from two or more sources. For example, a mixed sample may be a maternal sample comprising both maternal and fetal nucleic acids, e.g., maternal plasma, maternal serum, or maternal blood. A mixed sample from a transplant patient would be any fluid or tissue which contains biomolecules from both the donor cells and the cells of the patient. A mixed sample from a patient with a malignancy would contain biomolecules from the patient's normal, healthy tissue as well as biomolecules from the cancerous cells.

In a preferred aspect, the biomolecules analyzed are nucleic acids, e.g., RNA or DNA. In a more preferred aspect, the biomolecules analyzed comprise cell free nucleic acids. In a specific aspect, the biomolecules analyzed using the processing system of the invention comprise cell free DNA.

In preferred aspects, the frequency of two or more selected biomolecules (e.g., nucleic acids) within a sample are compared to identify the risk of a medical condition, and the probability of such risk is statistically informed by data on the biomolecule source contribution (e.g., the percentage of nucleic acids from a single source within the total nucleic acid population in the sample). In some aspects, the data on biomolecule source contribution in the sample can be incorporated into the initial probability calculation along with frequency data generated by comparison of the frequency of selected biomolecules in the sample. In another aspect, an initial risk probability for a medical condition may be calculated based on a comparison of frequencies of selected biomolecules in a mixed sample, and this initial probability subsequently adjusted based on the biomolecule source contribution of at least one source in the sample. In yet another aspect, the biomolecule source contribution is first determined for a mixed sample, and an expected risk probability is calculated for that sample based on the biomolecule populations. The expected risk probability can then be compared to the frequency of selected biomolecules in a mixed sample to determine the estimated probability of a medical condition. Alternatively, the biomolecule source contribution can be used to calculate risk expectation for two or more clinical states, and the frequency of selected molecules can be used to determine whether a particular mixed sample is more likely to be consistent with one clinical status versus another.

The frequency of the selected biomolecules used in the risk calculation can be determined using a variety of techniques, as described in more detail herein. The processes for detection include polymorphic detection, such as SNP detection of specific nucleic acids, or preferably non-polymorphic detection based on sequences or structural aspects of the biomolecules. Such frequency measurements are preferably total frequencies of the selected biomolecule in the sample regardless of the source, and thus it is not required that the selected biomolecules be distinguished as being from different sources prior to the use in the risk probability calculation. In one specific aspect, the biomolecules can be selected from a sample prior to detection, i.e. selectively isolated from a mixed sample prior to detection using amplification or capture techniques such as hybridization. In another specific aspect, the biomolecules may be selected after detection, e.g., by filtering frequency data generated from techniques such as massively parallel shotgun sequencing of nucleic acids within the mixed sample.

In certain aspects, the processes of the invention utilize the frequency of sets of selected biomolecules (e.g., nucleic acids) to identify copy number variations between a first and second source within the mixed sample. For example, a first set of nucleic acids may correspond to a first genomic region, a second set of nucleic acids may correspond to a second genomic region, and the combined frequencies from both the first and second source for each set can be compared to determine the presence or absence of a copy number variation in the first or second genomic region. In another example, multiple sets corresponding to different genomic regions from the first and second source can be used to determine the copy number variation of a larger genomic region which includes two or more smaller genomic regions. In yet another example, a first set of nucleic acids correspond to a first chromosome, a second set of nucleic acids correspond to a second chromosome, and the combined frequencies from both the first and second source for each set can be compared to determine the presence or absence of an aneuploidy in the first or second chromosome in a single source in a mixed sample.

Biomolecule source contribution can be determined using a number of different mechanisms that can distinguish biomolecules from two or more sources in a mixed sample. Such methods include detection of polymorphic differences in nucleic acids, epigenetic differences in nucleic acids (e.g., methylation), detection of certain genetic or structural differences between source biomolecules, etc.

In specific aspects, the risk probability calculations include ancillary information, e.g., medical information that may alter the risk profile of the patient for the particular medical condition. For example, the risk probability calculation for a maternal sample may include information on maternal age, gestational age of the fetus, or prior results from a screening test (e.g., serum screening such as the triple or quadruple screen) or medical procedure (e.g., ultrasound). In another example, the risk probability calculation for a patient with a malignancy may include information on biochemical markers such as the presence or absence of the estrogen receptor, HER-2/Neu, or progesterone receptor.

In one specific implementation, the invention provides a computer-implemented process for producing risk probabilities of a medical condition, comprising the steps of: determining the frequency of a first set of two or more biomolecules from a first genomic region in a mixed sample; determining the frequency of a second set of two or more biomolecules from a second genomic region in a mixed sample; determining a biomolecule source contribution for at least a first source in the mixed sample; and calculating an initial risk probability for a medical condition by comparing the frequency of the first and second sets in view of the biomolecule source contribution of the first source.

In another specific implementation, the invention provides a computer-implemented process for producing risk probabilities for a medical condition, comprising the steps of: inputting the frequency for a first set of two or more biomolecules from a first genomic region in a first and a second source in a mixed sample; inputting the frequency for a second set of two or more biomolecules from a second genomic region in a first and a second source in a mixed sample; calculating an initial risk probability for a medical condition by comparing the first and second sets; inputting the biomolecule source contribution from at least a first source in the mixed sample; and adjusting the risk probability based on the biomolecule source contribution.

In yet another specific implementation, the invention provides an executable software product stored on a computer-readable medium containing program instructions for calculating a risk probability for a medical condition, the program comprising instructions for inputting the frequency of a first set of two or more biomolecules from a first genomic region in a mixed sample; inputting the frequency of a second set of two or more biomolecules from a second genomic region in a mixed sample; inputting the biomolecule source contribution from at least a first source in the mixed sample; and calculating an initial risk probability for a medical condition by comparing the frequency of the first and second sets in view of the biomolecule source contribution.

In still another specific implementation, the invention provides an executable software product stored on a computer-readable medium containing program instructions for calculating a risk probability for a medical condition, the program comprising instructions for inputting the frequency of a first set of two or more biomolecules from a first genomic region in a mixed sample; inputting the frequency data for a second set of two or more biomolecules from a second genomic region in a mixed sample; calculating an initial risk probability for a medical condition by comparing the frequency of the first and second sets; inputting data on the biomolecule source contribution from at least a first source in the mixed sample; and adjusting the risk probability based on the biomolecule source contribution.

In more specific implementations, the invention provides products that comprise both software and hardware components. Thus, in a first such implementation, the invention provides an executable software product stored on a computer-readable medium containing program instructions for calculating a risk probability for a medical condition, the program comprising instructions for a memory; a processor coupled to the memory; and a software component executed by the processor that is configured to receive a first data set comprising frequency of a first set of two or more biomolecules from a first genomic region in a mixed sample, receive a second data set comprising frequency of a second set of two or more biomolecules from a second genomic region in a mixed sample, receive a third data set comprising a biomolecule source contribution from at least a first source in the mixed sample; and calculate a risk probability for a medical condition based on a comparison of the frequency of the first and second sets of biomolecules in view of the third data set.

In another implementation, the invention provides an executable software product stored on a computer-readable medium containing program instructions for calculating a risk probability for a medical condition, the program comprising instructions for a memory; a processor coupled to the memory; and a software component executed by the processor that is configured to receive a first data set comprising frequency of a first set of two or more biomolecules from a first genomic region in a first and second source in a mixed sample, receive a second data set comprising frequency data for a second set of two or more biomolecules from a second genomic region in a first and second source in a mixed sample, calculate a risk probability for a medical condition based on a comparison of the frequency of the first and second sets of biomolecules, receive a third data set comprising a biomolecule source contribution from one or more sources in the mixed sample; and adjust the calculated risk probability based on the biomolecule source contribution.

In yet another implementation, the invention provides a computer software product including a non-transitory computer-readable storage medium having fixed therein a sequence of instructions which when executed by a computer direct performance of steps of receiving a first data set comprising frequency data for a first set of two or more biomolecules from a first genomic region in a mixed sample, receiving a second data set comprising frequency data for a second set of two or more biomolecules from a second genomic region in a mixed sample, receiving a third data set comprising a biomolecule source contribution from one or more sources in the mixed sample and calculating a risk probability for a medical condition based on a comparison of the frequency of the first and second sets of biomolecules in view of the biomolecule source contribution in the mixed sample.

In still another implementation, the invention provides a computer software product including a non-transitory computer-readable storage medium having fixed therein a sequence of instructions which when executed by a computer direct performance of steps of receiving a first data set comprising frequency data for a first set of two or more biomolecules from a first genomic region in a mixed sample; receiving a second data set comprising frequency data for a second set of two or more biomolecules from a second genomic region in a mixed sample, calculating a risk probability for a medical condition based on a comparison of the frequency of the first and second sets of biomolecules, receiving a third data set comprising a biomolecule source contribution from one or more sources in the mixed sample, and adjusting the calculated risk probability based on the biomolecule source contribution.

In certain aspects, the invention provides systems with the ability to execute the processes and products of the invention. Thus, in one implementation, the invention provides a memory; a processor coupled to the memory; and a software component executed by the processor that is configured to receive a first data set comprising frequency data for a first set of two or more biomolecules from a first genomic region in a mixed sample, receive a second data set comprising frequency data for a second set of two or more biomolecules from a second genomic region in a mixed sample, receive a third data set comprising a biomolecule source contribution from one or more sources in the mixed sample and calculate a risk probability for a medical condition based on a comparison of the frequency of the first and second sets of biomolecules in view of the third data set.

In another implementation, the invention comprises a system, comprising a memory; a processor coupled to the memory; and a software component executed by the processor that is configured to receive a first data set comprising frequency data for a first set of two or more biomolecules in a mixed sample, receive a second data set comprising frequency data for a second set of two or more biomolecules in a mixed sample, calculate a risk probability for a medical condition based on a comparison of the frequency of the first and second sets of biomolecules, receive a third data set comprising a biomolecule source contribution from one or more sources in the mixed sample; and adjust the risk probability based on the biomolecule source contribution.

Exemplary mixed samples for analysis using the invention include samples comprising both maternal and fetal biomolecules, samples that contain genetic material from normal cells and circulating cancerous cells, and samples that contain genetic material from a transplant patient and from an allogeneic donated organ within the transplant patient.

In one specific aspect, the mixed sample is a maternal sample, and the biomolecules detected are cell free nucleic acids. Determining the maternal and/or fetal source contribution in a maternal sample informs the statistical calculation of chromosomal abnormalities of the mother and/or preferably of the fetus.

In another specific aspect, the mixed sample is a maternal sample comprising both maternal and fetal cells. The sample may be enriched for fetal cells prior to execution of the processes of the invention.

In another specific aspect the biomolecules measured in a mixed sample comprise genomic material (e.g., cell free DNA) from both normal and putative genetically atypical cells.

In preferred aspects, the biomolecules are nucleic acids, and the frequency of a biomolecule in a mixed sample is quantified through sequence determination of the biomolecules or nucleic acid products corresponding to the biomolecules in the mixed sample. In more preferred aspects, the biomolecules are selectively amplified prior to sequence determination. In other aspects, the sequence of the biomolecules is determined through massively parallel shotgun sequencing. In yet other aspects, the frequency of the biomolecules is quantified using digital PCR.

In certain aspects, the sets of biomolecules are sets of nucleic acids corresponding to a genomic region in the mixed sample. In more specific aspects, the sets of biomolecules correspond to a particular chromosome, and the frequencies are compared to determine the risk probability of copy number variation or chromosome abnormality (e.g., an aneuploidy). Frequencies can be compared between sets of biomolecules to determine risk probability for the presence of a copy number variation or a chromosome abnormality. Such frequencies in sets of biomolecules may also be compared to reference frequencies to determine the risk probability, e.g., for the presence or absence of a copy number variation or a chromosome abnormality.

In one aspect, the processing system utilizes detection of nucleic acid regions in cell free DNA in a mixed sample to identify the presence or absence of a chromosomal aneuploidy. Frequency data for a selected biomolecule can be determined by detection of genomic region of interest (e.g., a chromosome or a portion thereof) and compared to the quantities of one or more other genomic regions of interest and/or one or more reference genomic regions from other biomolecules, e.g., to detect potential aneuploidies based on chromosome frequencies in the mixed sample. The biomolecule of interest may be selected prior to detection, or the biomolecule population of a sample may be detected (e.g., using whole genome sequencing) and the frequency of specific genomic regions may be identified utilizing the detected population.

These and other aspects, features and advantages will be provided in more detail as described herein.

DESCRIPTION OF THE FIGURES

FIG. 2 is a table with demographics of the subjects from which maternal samples were obtained and analyzed in the Examples.

DETAILED DESCRIPTION OF THE INVENTION

Figure 1:
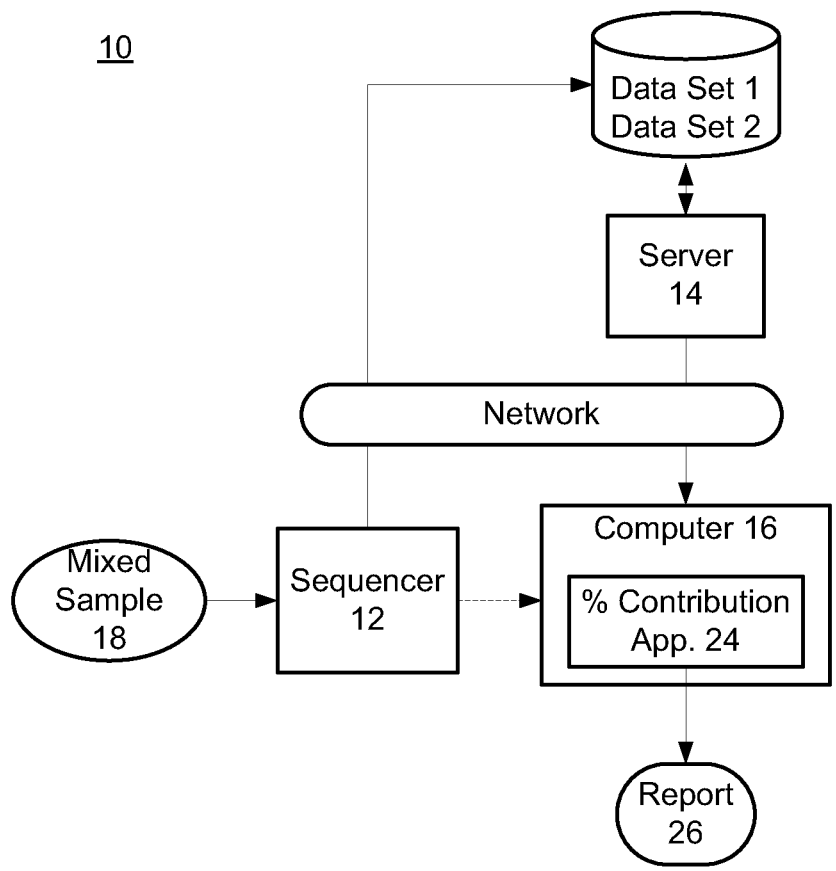
FIG. 1 is a block diagram illustrating an exemplary system environment.

The processes described herein may employ, unless otherwise indicated, conventional techniques and descriptions of molecular biology (including recombinant techniques), genomics, biochemistry, and sequencing technology, which are within the skill of those who practice in the art. Such conventional techniques include hybridization and ligation of oligonucleotides, next generation sequencing, and detection of hybridization using a label. Specific illustrations of suitable techniques can be had by reference to the examples herein. However, equivalent conventional procedures can, of course, also be used. Such conventional techniques and descriptions can be found in standard laboratory manuals such as Green, et al., Eds., *Genome Analysis: A Laboratory Manual Series* (Vols. I-IV) (1999); Weiner, et al., Eds., *Genetic Variation: A Laboratory Manual* (2007); Dieffenbach, Dveksler, Eds., *PCR Primer: A Laboratory Manual* (2003); Bowtell and Sambrook, *DNA Microarrays: A Molecular Cloning Manual* (2003); Mount, *Bioinformatics: Sequence and Genome Analysis* (2004); Sambrook and Russell, *Condensed Protocols from Molecular Cloning: A Laboratory Manual* (2006); and Sambrook and Russell, *Molecular Cloning: A Laboratory Manual* (2002) (all from Cold Spring Harbor Laboratory Press); Stryer, L., *Biochemistry* (4th Ed.) W. H. Freeman, New York (1995); Gait, "*Oligonucleotide Synthesis: A Practical Approach*" IRL Press, London (1984); Nelson and Cox, *Lehninger, Principles of Biochemistry*, $3^{rd}$ Ed., W.H. Freeman Pub., New York (2000); and Berg et al., *Biochemistry*, $5^{th}$ Ed., W.H. Freeman Pub., New York (2002), all of which are herein incorporated by reference in their entirety for all purposes. Before the present compositions, research tools and processes are described, it is to be understood that this invention is not limited to the specific processes, compositions, targets and uses described, as such may, of course, vary. It is also to be understood that the terminology used herein is for the purpose of describing particular aspects only and is not intended to limit the scope of the present invention, which will be limited only by appended claims.

It should be noted that as used herein and in the appended claims, the singular forms "a," "and," and "the" include plural referents unless the context clearly dictates otherwise. Thus, for example, reference to "a nucleic acid region" refers to one, more than one, or mixtures of such regions, and reference to "an assay" includes reference to equivalent steps and processes known to those skilled in the art, and so forth.

Where a range of values is provided, it is to be understood that each intervening value between the upper and lower limit of that range—and any other stated or intervening value in that stated range—is encompassed within the invention. Where the stated range includes upper and lower limits, ranges excluding either of those included limits are also included in the invention.

Unless expressly stated, the terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated. All publications mentioned herein, and in particular patent applications and issued patents, are incorporated by reference for the purpose of describing and disclosing various aspects, details and uses of the processes and systems that are described in the publication and which might be used in connection with the presently described invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

DEFINITIONS

The terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated.

The term "amplified nucleic acid" is any nucleic acid molecule whose amount has been increased at least two fold by any nucleic acid amplification or replication process performed in vitro as compared to its starting amount in a maternal sample.

The term "biomolecule source population" refers to the estimated percentage of biomolecules in a sample that are from a particular source compared to the total number of biomolecules in the mixed sample.

The term "chromosomal abnormality" refers to any genetic variant for all or part of a chromosome. The genetic variants may include but not be limited to any copy number variant such as aneuploidy, duplications or deletions, translocations, inversions, and mutations.

The term "diagnostic tool" as used herein refers to any composition or assay of the invention used in combination as, for example, in a system in order to carry out a diagnostic test or assay on a patient sample.

The term "distinguishing region" refers to a region that is measurably different between loci. Such differences include, but are not limited to, single nucleotide polymorphisms (SNPs), differences in methylation status, mutations including point mutations and indels, short tandem repeats, copy number variants, and the like.

The term "hybridization" generally means the reaction by which the pairing of complementary strands of nucleic acid occurs. DNA is usually double-stranded, and when the strands are separated they will re-hybridize under the appropriate conditions. Hybrids can form between DNA-DNA, DNA-RNA or RNA-RNA. They can form between a short strand and a long strand containing a region complementary to the short one. Imperfect hybrids can also form, but the more imperfect they are, the less stable they will be (and the less likely to form).

The terms "locus" and "loci" as used herein refer to a nucleic acid region of known location in a genome.

The term "informative locus" as used herein refers to a locus with one or more distinguishing regions which is homozygous in one source and heterozygous in another source within a mixed sample.

The term "maternal sample" as used herein refers to any sample taken from a pregnant mammal which comprises a maternal major source and a fetal minor source of nucleic acids (e.g., RNA or DNA).

The term "mixed sample" as used herein refers to any sample comprising nucleic acids (e.g., RNA or DNA) from two or more sources in a single individual. Exemplary mixed samples include a maternal sample (e.g., maternal blood, serum or plasma comprising both maternal and fetal cells, RNA and/or DNA), and a peripherally-derived somatic sample (e.g., blood, serum or plasma comprising different cell types, e.g., hematopoietic cells, mesenchymal cells, and circulating cells from other organ systems). Mixed samples include samples with biomolecules from two different sources, which may be sources derived from the single individual, e.g., normal and atypical somatic cells; biomolecules derived from two different subjects within the single individual, e.g., a sample with both maternal and fetal genomic material or a sample from a transplant patient that comprises cells from both the donor and recipient; or samples with nucleic acids from two or more sources from different organisms within the single individual, e.g., the mammalian host and an infectious organism such as a virus, bacteria, fungus, parasite, etc.

As used herein "polymerase chain reaction" or "PCR" refers to a technique for replicating a specific piece of target DNA in vitro, even in the presence of excess non-specific DNA. Primers are added to the target DNA, where the primers initiate the copying of the target DNA using nucleotides and, typically, Taq polymerase or the like. By cycling the temperature, the target DNA is repetitively denatured and copied. A single copy of the target DNA, even if mixed in with other, random DNA, can be amplified to obtain billions of replicates. The polymerase chain reaction can be used to detect and measure very small amounts of DNA and to create customized pieces of DNA. In some instances, linear amplification processes may be used as an alternative to PCR.

The term "polymorphism" as used herein refers to any genetic changes in a loci that may be indicative of that particular loci, including but not limited to single nucleotide polymorphisms (SNPs), methylation differences, short tandem repeats (STRs), and the like.

Generally, a "primer" is an oligonucleotide used to, e.g., prime DNA extension, ligation and/or synthesis, such as in the synthesis step of the polymerase chain reaction or in the primer extension techniques used in certain sequencing reactions. A primer may also be used in hybridization techniques as a means to provide complementarity of a nucleic acid region to a capture oligonucleoitide for detection of a specific nucleic acid region.

The term "research tool" as used herein refers to any composition or assay of the invention used for scientific enquiry, academic or commercial in nature, including the development of pharmaceutical and/or biological therapeutics. The research tools of the invention are not intended to be therapeutic or to be subject to regulatory approval; rather, the research tools of the invention are intended to facilitate research and aid in such development activities, including any activities performed with the intention to produce information to support a regulatory submission.

The term "selected nucleic acid region" as used herein refers to a nucleic acid region corresponding to an individual chromosome. Such selected nucleic acid regions may be directly isolated and enriched from the sample for detection, e.g., based on hybridization and/or other sequence-based techniques, or they may be amplified using the sample as a template prior to detection of the sequence. Nucleic acids regions for use in the processing systems of the present invention may be selected on the basis of DNA level variation between individuals, based upon specificity for a particular chromosome, based on CG content and/or required amplification conditions of the selected nucleic acid regions, or other characteristics that will be apparent to one skilled in the art upon reading the present disclosure.

The terms "sequencing", "sequence determination" and the like as used herein refers generally to any and all biochemical processes that may be used to determine the order of nucleotide bases in a nucleic acid.

The term "specifically binds", "specific binding" and the like as used herein, when referring to a binding partner (e.g., a nucleic acid probe or primer, antibody, etc.) that results in the generation of a statistically significant positive signal under the designated assay conditions. Typically the interaction will subsequently result in a detectable signal that is at least twice the standard deviation of any signal generated as a result of undesired interactions (background).

The Invention in General

Including biomolecule source contribution in the risk calculation of medical conditions allows a more accurate determination of the risk calculation than a risk calculation based only on the frequency determination for selected biomolecules in the sample. The risk probabilities determined using the processes of the invention are achieved using computer-implemented calculations of risk probabilities based on the number of standard deviations from the mean to the probabilistic value of interest. Exemplary statistical techniques used include, but are not limited to, Z tests of proportions, Wald tests, bootstrapping, and Bayesian modeling.

The estimated levels of biomolecule populations from the different sources within a mixed sample provides important information on the expected statistical presence of one or more selected biomolecule that is informative of a medical condition within the sample, and provides for the calculation of more accurate risk probabilities for the presence or absence of the particular medical condition based on deviations from the expected frequencies. Combining the frequency information of the biomolecule populations from different sources within a population and the data on specific biomolecules associated with a medical condition informs the statistical probability of a medical condition based on deviation from expected frequencies of specific biomolecules from a single source within the mixed sample, and provides a much more accurate assessment of the risk probabilities for the identification of a medical condition. Thus, deviation from the frequency expectation of the selected biomolecules in view of the biomolecule source population can be indicative of the risk of a particular medical condition.

The biomolecule source contribution can be determined using any reasonable estimation of the levels of biomolecules from a single source in a mixed sample. This includes identification based on biochemical differences between biomolecules from different sources (e.g., differences in methylation), differences in physical composition between biomolecules from different sources, sequence differences between biomolecules from different sources, overall size differences in biomolecule populations from a source, or other methods for distinguishing and/or estimating the populations of one source from another can be used to determine the biomolecule source contribution. In a specific aspect, the biomolecules populations are nucleic acids, and the population contributions are determined based on differences in nucleic acid composition (e.g., single nucleotide polymorphisms, short tandem repeats, etc.) between biomolecules in a first and a second source.

FIG. 1 is a block diagram illustrating an exemplary system environment in which one embodiment of the present invention may be implemented for determining contribution of cell free nucleic acids from the major source and/or minor source in a mixed sample. The system 10 includes a DNA sequencer 12, a server 14 and a computer 16. The DNA sequencer 12 may be coupled to the server 14 and/or the computer directly or through a network. The computer 16 may be in communication with the server 14 through the same or different network.

In one embodiment, a mixed sample 18 is input to the DNA sequencer 12. In one embodiment, the mixed sample 18 may comprise genetic material from maternal and fetal sources. The DNA sequencer 12 may be any commercially available instrument that automates the DNA sequencing process for sequence analysis of oligonucleotides present in the mixed sample 18. The output of the DNA sequencer 12 may be in the form of first and second data sets 20 comprising frequency data for one or more informed and loci from major and minor sources. In one embodiment, the first and second data sets 20 may be stored in a database 22 that is accessible by the server 14.

According to the exemplary embodiment, the computer 16 executes a software component, referred to herein as the risk probability calculation application 24, that calculates an estimated contribution of cell free nucleic acids from at least one source based on distinguishing regions from the first and second data sets of the mixed sample 18. In one embodiment, the computer 16 may comprise a personal computer, but the computer 16 may comprise any type of machine that includes at least one processor and memory.

The output of the risk probability calculation application 24 is a report 26 listing estimated contribution of cell free nucleic acids. The report 26 may be paper that is printed out, or electronic, which may be displayed on a monitor and/or communicated electronically to users via e-mail, FTP, text messaging, posted on a server, and the like.

Although the risk probability calculation application 24 is shown as being implemented as software, the risk probability calculation application 24 may be implemented as a combination of hardware and software. In addition, the risk probability calculation application 24 may be implemented as multiple components operating on the same or different computers.

Both the server 14 and the computer 16 may include hardware components of typical computing devices (not shown), including a processor, input devices (e.g., keyboard, pointing device, microphone for voice commands, buttons, touchscreen, etc.), and output devices (e.g., a display device, speakers, and the like). The server 14 and computer 16 may include computer-readable media, e.g., memory and storage devices (e.g., flash memory, hard drive, optical disk drive, magnetic disk drive, and the like) containing computer instructions that implement the functionality disclosed when executed by the processor. The server 14 and the computer 16 may further include wired or wireless network communication interfaces for communication.

Although the server 14 and computer 16 are shown as single computers, it should be understood that they could be multiple servers and computers, and the functionality of the risk probability calculation application 24 may be implemented using a different number of software components. For example, the risk probability calculation application 24 may be implemented as more than one component.

Determination of Biomolecule Source Contribution in a Maternal Sample

In certain specific aspects, determining the percentage of fetal DNA in a maternal sample may be beneficial in risk calculation, as it provides important information on the expected statistical presence of chromosomes where variation from that expectation may be indicative of fetal aneuploidy. This may be especially helpful in circumstances where the level of fetal DNA in a maternal sample is low, as the percent fetal contribution can be used in determining the quantitative statistical significance in the variations of levels of identified nucleic acid regions in a maternal sample. Knowledge of the fetal DNA percentage or amount may be used to determine whether any other analysis on the sample can be performed. It may be the case at a certain lower bound of fetal DNA amount, the processing system is not able to reliably perform analysis. In other aspects, determination of the percent fetal cell free DNA in a maternal sample may be beneficial in estimating the level of certainty or power in detecting a fetal aneuploidy.

In some specific aspects, the fetal contribution of maternal DNA at the allele of interest can be compared to the non-maternal contribution at that allele to determine approximate fetal DNA concentration in the sample. In other specific aspects, the quantity of solely paternally-derived sequences (e.g., Y-chromosome sequences or paternal-specific polymorphisms) can be used to determine the concentration of fetal DNA in a maternal sample.

Another exemplary approach to determining the percent fetal contribution in a maternal sample is through the analysis of nucleic acid fragments e.g., cell free DNA, with different patterns of DNA methylation between fetal and maternal DNA.

Determination of Fetal DNA Content in a Maternal Sample Using Y-Specific Sequences In circumstances where the fetus is male, percent fetal DNA in a sample can be determined through detection of Y-specific nucleic acids and comparison to calculated maternal DNA content.

For example, quantities of an amplified Y-specific nucleic acid, such as a region from the sex-determining region Y gene (SRY), which is located on the Y chromosome and is thus representative of fetal DNA, can be determined from the sample and compared to one or more amplified genomic regions which are present in both maternal DNA and fetal DNA and which are preferably not from a chromosome believed to potentially be aneuploid in the fetus, e.g., an autosomal region that is not on chromosome 21 or 18. Preferably, this amplification step is performed in parallel with the selective amplification step, although it may be performed either before or after the selective amplification depending on the nature of the multiplexed assay.

In another example, the fetal DNA concentration in a sample is calculated using methods that take into account the small percentage of background maternal DNA that may be incorrectly identified as originating from chromosome Y. Specifically, using certain bioinformatics algorithms, a small number of DNA molecules are incorrectly identified as originating from chromosome Y in pregnancies with female fetuses. Chiu R W K, et al. *Proc Natl Acad Sci USA* 2008; 105:20458-63. The % chrY value in a pregnancy with a male fetus is thus a composite of the amount of chromosome Y sequences contributed by the male fetus and those sequences from the maternal background DNA that were incorrectly assigned to chromosome Y. Accordingly, in certain aspects, the fetal DNA concentration can be more correctly derived from the equation: chrY %=0.157F+0.007(1−F). Chiu R W K, et al., BMJ 2011; 342:c7401.

In a preferred aspect, the amplified DNA from plasma free DNA is produced by the polymerase chain reaction (PCR). Other mechanisms for amplification can be used as well, including those described in more detail herein, as will be apparent to one skilled in the art upon reading the present disclosure.

In particular aspects, the percentage of free fetal DNA in the maternal sample can determined by PCR using serially diluted DNA isolated from the maternal sample, which can accurately quantify the number of genomes comprising the amplified genes. For example, if the blood sample contains 100% male fetal DNA, and 1:2 serial dilutions are performed, then on average the SRY signal will disappear 1 dilution before the autosomal signal, since there is 1 copy of the SRY gene and 2 copies of the autosomal gene.

In a specific aspect, the percentage of free fetal DNA in maternal plasma is calculated using the following formula: percentage of free fetal DNA=(No. of copies of SRY gene× 2×100)/(No. of copies of autosomal gene), where the number of copies of each gene is determined by observing the highest serial dilution in which the gene was detected. The formula contains a multiplication factor of 2, which is used to normalize for the fact that there is only 1 copy of the SRY gene compared to two copies of the autosomal gene in each genome, fetal or maternal.

Determination of Fetal DNA Content in a Maternal Sample Using Fetal Autosomal Polymorphisms and Genetic Variations In each maternally-derived sample, the DNA from a fetus will have approximately 50% of its loci inherited from the mother and approximately 50% of the loci are non-maternal. Determining the loci contributed to the fetus from non-maternal sources can allow the estimation of fetal DNA in a maternal sample, and thus provide information used to calculate the statistically significant differences in chromosomal frequencies for chromosomes of interest.

In certain aspects, the determination of fetal polymorphisms requires targeted SNP and/or mutation analysis to identify the presence of fetal DNA in a maternal sample. In some aspects, the use of prior genotyping of the father and mother can be performed. For example, the parents may have undergone such genotype determination for identification of disease markers, e.g., determination of the genotype for disorders such as cystic fibrosis, muscular dystrophy, spinal muscular atrophy or even the status of the RhD gene. Such difference in polymorphisms, copy number variants or mutations can be used to determine the percentage fetal contribution in a maternal sample.

In one preferred aspect, the percent fetal cell free DNA in a maternal sample can be quantified using multiplexed SNP detection without using prior knowledge of the maternal or paternal genotype. In this aspect, two or more selected polymorphic nucleic acid regions with a known SNP in each region are used. In a preferred aspect, the selected polymorphic nucleic acid regions are located on an autosomal chromosome that is unlikely to be aneuploid, e.g. Chromosome 2. The selected polymorphic nucleic acid regions from the maternal specimen (e.g. plasma) are amplified. In a preferred aspect, the amplification is universal. In a preferred embodiment, the selected polymorphic nucleic acid regions are amplified in one reaction in one vessel. In a preferred aspect, the selected polymorphic nucleic acid regions and the selected non-polymorphic nucleic acids in the genomic regions of interest are amplified together in one reaction in on one vessel. Each allele of the selected polymorphic nucleic acid regions in the maternal sample is determined and quantified. In a preferred aspect, high throughput sequencing is used for such determination and quantification. Loci are identified where the maternal and fetal genotypes are different, e.g., the maternal genotype is homozygous and the fetal genotype is heterozygous. This identification is done by observing a high frequency of one allele (>80%) and a low frequency (<20% and >0.15%) of the other allele for a particular selected nucleic acid region. The use of multiple loci is particularly advantageous as it reduces the amount of variation in the measurement of the abundance of the alleles between loci. All or a subset of the loci that meet this requirement are used to determine fetal contribution through statistical analysis. In one aspect, fetal contribution is determined by summing the low frequency alleles from two or more loci together, dividing by the sum of the low and high frequency alleles and multiplying by two.

For many alleles, maternal and fetal sequences may be homozygous and identical, and as this information therefore does not distinguishing between maternal and fetal DNA it is not useful in the determination of percent fetal DNA in a maternal sample. The present invention utilizes allelic information where there is a distinguishable difference between the fetal and maternal DNA (e.g., a fetal allele containing at least one allele that differs from the maternal allele) in calculations of percent fetal DNA. Data pertaining to allelic regions that are the same for the maternal and fetal DNA are thus not selected for analysis, or are removed from the pertinent data prior to determination of percentage fetal DNA so as not to swamp out mask the useful data.

Exemplary processes for quantifying fetal DNA in maternal plasma can be found, e.g., in Chu et al., *Prenat Diagn* 2010; 30:1226-1229, which is incorporated herein by reference.

In one aspect, selected nucleic acid regions may be excluded if the amount or frequency of the region appears to be an outlier due to experimental error, or from idiopathic genetic bias within a particular sample. In another aspect, selected nucleic acids may undergo statistical or mathematical adjustment such as normalization, standardization, clustering, or transformation prior to summation or averaging. In another aspect, selected nucleic acids may undergo both normalization and data experimental error exclusion prior to summation or averaging.

In a preferred aspect, 12 or more loci are used for the analysis. In another preferred aspect, 24 or more loci are used for the analysis. In another preferred aspect, 48 or more loci are used for the analysis. In another aspect, one or more indices are used to identify the sample, the locus, the allele or the identification of the nucleic acid.

In one preferred aspect, the percentage fetal contribution in a maternal sample can be quantified using tandem SNP detection in the maternal and fetal alleles. Techniques for identifying tandem SNPs in DNA extracted from a maternal sample are disclosed in Mitchell et al, U.S. Pat. No. 7,799,531 and U.S. patent application Ser. Nos. 12/581,070, 12/581,083, 12/689,924, and 12/850,588. These describe the differentiation of fetal and maternal loci through detection of at least one tandem single nucleotide polymorphism (SNP) in a maternal sample that has a different haplotype between the fetal and maternal genome. Identification and quantification of these haplotypes can be performed directly on the maternal sample, as described in the Mitchell et al. disclosures, and used to determine the percent fetal contribution in the maternal sample.

Determination of Fetal DNA Content in a Maternal Sample Using Epigenetic Allelic Ratios Certain genes have been identified as having epigenetic differences between the placenta and maternal blood cells, and such genes are candidate loci for fetal DNA markers in a maternal sample. See, e.g., Chim S S C, et al. *Proc Natl Acad Sci USA* (2005); 102:14753-14758. These loci, which are unmethylated in the placenta but not in maternal blood cells, can be readily detected in maternal plasma and were confirmed to be fetus specific. The comparison of methylated and unmethylated amplification products in a maternal sample can be used to quantify the percent fetal DNA contribution to the maternal sample by calculating the epigenetic allelic ratio for one or more of such sequences known to be differentially-methylated in fetal DNA as compared to maternal DNA.

To determine methylation status of nucleic acids in a maternal sample, the nucleic acids of the sample are subjected to bisulfite conversion. Conventional processes for such bisulphite conversion include, but are not limited to, use of commercially available kits such as the Methylamp™ DNA Modification Kit (Epigentek, Brooklyn, N.Y.). Allelic frequencies and ratios can be directly calculated and exported from the data to determine the percentage of fetal DNA in the maternal sample.

Detection of Selected Biomolecules Associated with a Medical Condition

The biomolecule levels that are used for comparison for detection of chromosomal abnormalities (e.g., aneuploidies) can be detected using a number of different techniques known to those skilled in the art. Exemplary techniques for identifying selected nucleic acids for providing the data on selected biomolecules for use in the processes of the invention are described below, and all references are incorporated for teaching the various methods one skilled in the art could use to obtain the biomolecule data for use in the present processes, products and systems.

In one aspect, the nucleic acid detection used to provide data on selected biomolecules utilizes analysis of random DNA segments is used, such as that described in, e.g., Quake et al., U.S. Pat. Nos. 8,008,018 and 7,888,017, and Shoemaker et al., which are incorporated herein by reference.

Briefly, the frequency of the biomolecules within a mixed sample can be differentially detected using target sequences. The genetic material may be genomic DNA or RNA, preferably mRNA. In the case of mRNA, one may choose target sequences corresponding to genes that are highly expressed in the minor source. Where the biomolecules are nucleic acids, the genetic material in each reaction sample is detected with a sequence specific reactant directed to at least one of two target sequences in the genetic material to obtain a detectable reaction product if the target sequence is present in the reaction sample. For example, when the mixed sample is a maternal sample interrogated for a chromosome abnormality, a probe specific to a chromosome is bound to the reaction sample, along with a control probe specific to another chromosome. In most cases, the results will be from maternal nucleic acids, but a small number of results will be obtained from fetal nucleic acids. In order to distinguish random variation from fetal results, a large number of reactions are run, and statistical processes are applied to the results. The labeling and detection in the present process is used to distinguish the presence or absence of a single target sequence, referred to as "digital analysis," although it may be performed with sensitive nucleic acid detection processes which distinguish between one and more than one target sequence in a discrete sample.

In another example, massively parallel sequencing of nucleic acid biomolecules (e.g., DNA fragments randomly selected from the sample) is used to determine the sequence of said biomolecules and identification of the frequency of the biomolecules within the mixed sample. For detection of a chromosome frequency abnormality (e.g., a trisomy), the sequenced biomolecules are identified as being from a first chromosome, and the total amounts of biomolecules from at least one first chromosome in said mixed sample are compared to total amounts of biomolecules from at least one second chromosome in said mixed sample. The total amounts include the biomolecules from both a first and a second source in the mixed sample, and the biomolecules from the first source are not differentiated from the second source in determining the frequency of the biomolecules corresponding to the chromosome frequency. Where one first chromosome is presumed to be euploid, and the second chromosome is suspected to be aneuploid, the total numbers of biomolecules for the first and second biomolecules are compared to determine the presence or absence of said aneuploidy.

In more specific aspects, the samples used for massively parallel sequencing of nucleic acid biomolecules are enriched for polymorphic regions. Exemplary techniques for doing so include those disclosed in, e.g., WO2011091063, WO2011091046 and U.S. Pat Appln No. 20110230358. Briefly, a portion of a mixed sample comprising cell free DNA is amplified to augment the number of copies of the one or more polymorphic sequences in the sample, and added back to the original sample for sequencing. Alternatively, the sample subjected to whole genome sequencing to obtain a plurality of sequence tags, and the sequences of the tags are compared to the sequence of multiple reference polymorphisms.

In some aspects, the biomolecules are detected using array-based hybridization processes, such as those described in U.S. Pat. Appln No. 20110172111. In other aspects, the biomolecules are detected using nanopore technology detection, such as those described in U.S. Pat. Appln No. 20110124518.

In another aspect, the nucleic acids are detected and compared using polymorphisms that differentiate between maternal and fetal alleles in a sample, using methods described in U.S. Pat. Nos. 7,727,720, 7,718,370, 7,598,060, 7,442,506, 7,332,277, 7,208,274, and 6,977,162. Briefly, the methods utilize polymorphic detection to identify chromosomal abnormalities. Sequences are determined at alleles that are homozygous in the mother and heterozygous in the fetus, and a ratio for the heterozygous alleles are determined. The ratio for the heterozygous alleles is used to indicate the presence or absence of a chromosomal abnormality.

In yet another aspect, the nucleic acid detection used to provide data on selected biomolecules utilizes identification of tandem polymorphisms, such as that described in, e.g., U.S. Pat. No. 7,799,531, and U.S. application Ser. Nos. 20110117548, 20110059451, 20100184044, 2010184043, 20080020390. Briefly, tandem SNPs are detected and used to differentiate maternal and fetal alleles in a maternal sample to detect fetal chromosomal abnormalities through comparison of maternal DNA to fetal DNA.

In a preferred aspect, the nucleic acid detection used to provide data on selected biomolecules utilizes selected amplification of representative loci. Such techniques are disclosed in, e.g., U.S. application Ser. Nos. 13/013,732, 13/205,490, 13/205,570, and 13/205,603. These techniques utilize detection of genomic regions using fixed sequence oligonucleotides and joining them via ligation and/or extension. This can be accomplished using a combination of ligation and amplification, e.g., the ligation of two or more fixed sequence oligonucleotides and optionally a bridging oligonucleotide that is complementary to a region between the fixed sequence oligonucleotides.

In some embodiments, the biomolecules are derived from two distinct cell sources (e.g., fetal cells and maternal cells) within a mixed sample, optionally enriched for the minor cell source. The cells isolated from the mixed sample can be divided between two or more discrete locations that can be used as addressable locations, and the cells identified using labeling processes, e.g., unique tag sequences such as those taught in Shoemaker et al., U.S. patent application Ser. No. 12/230,628.

Once the comparators of the biomolecules associated with the medical condition are determined, the level of total biomolecules from the different sources is then used in the calculation of the risk probabilities of the medical condition.

In a preferred aspect, aneuploidy detection processes that utilize analysis of selected biomolecules (e.g., nucleic acid regions) from a mixed sample are used. In this aspect, the biomolecule source contribution is preferably the percent fetal cell free DNA calculated in the mixed sample. In one preferred aspect, the chromosomal ratio and its variation for the normal population are determined from normal samples that have a similar percentage of fetal DNA. An expected aneuploidy chromosomal ratio for a DNA sample with that percent fetal cell free DNA is calculated by adding the percent contribution from the aneuploidy chromosome. The chromosomal ratio for the sample may then be compared to the chromosomal ratio for the normal population and to the expected aneuploidy chromosomal ratio to determine statistically, using the variation of the chromosomal ratio, if the sample is more likely normal or aneuploid, and the statistical probability that it is one or the other.

In a preferred aspect, the selected regions of a mixed sample include both regions for determination of biomolecule source content as well as regions from selected biomolecules corresponding to two or more chromosomes to detect a chromosomal abnormality in a single reaction. The single reaction helps to minimize the risk of contamination or bias that may be introduced during various steps in the processing system which may otherwise skew results.

In other aspects, a selected region or regions may be utilized both for determination of fetal DNA content as well as detection of fetal chromosomal abnormalities. The alleles for selected regions can be used to determine fetal DNA content and these same selected regions can then be used to detect fetal chromosomal abnormalities ignoring the allelic information. Utilizing the same regions for both fetal DNA content and detection of chromosomal abnormalities may further help minimize any bias due to experimental error or contamination.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric.

Example 1

Identification of Non-Polymorphic Loci to be Used in Aneuploidy Analysis

Figure 2:
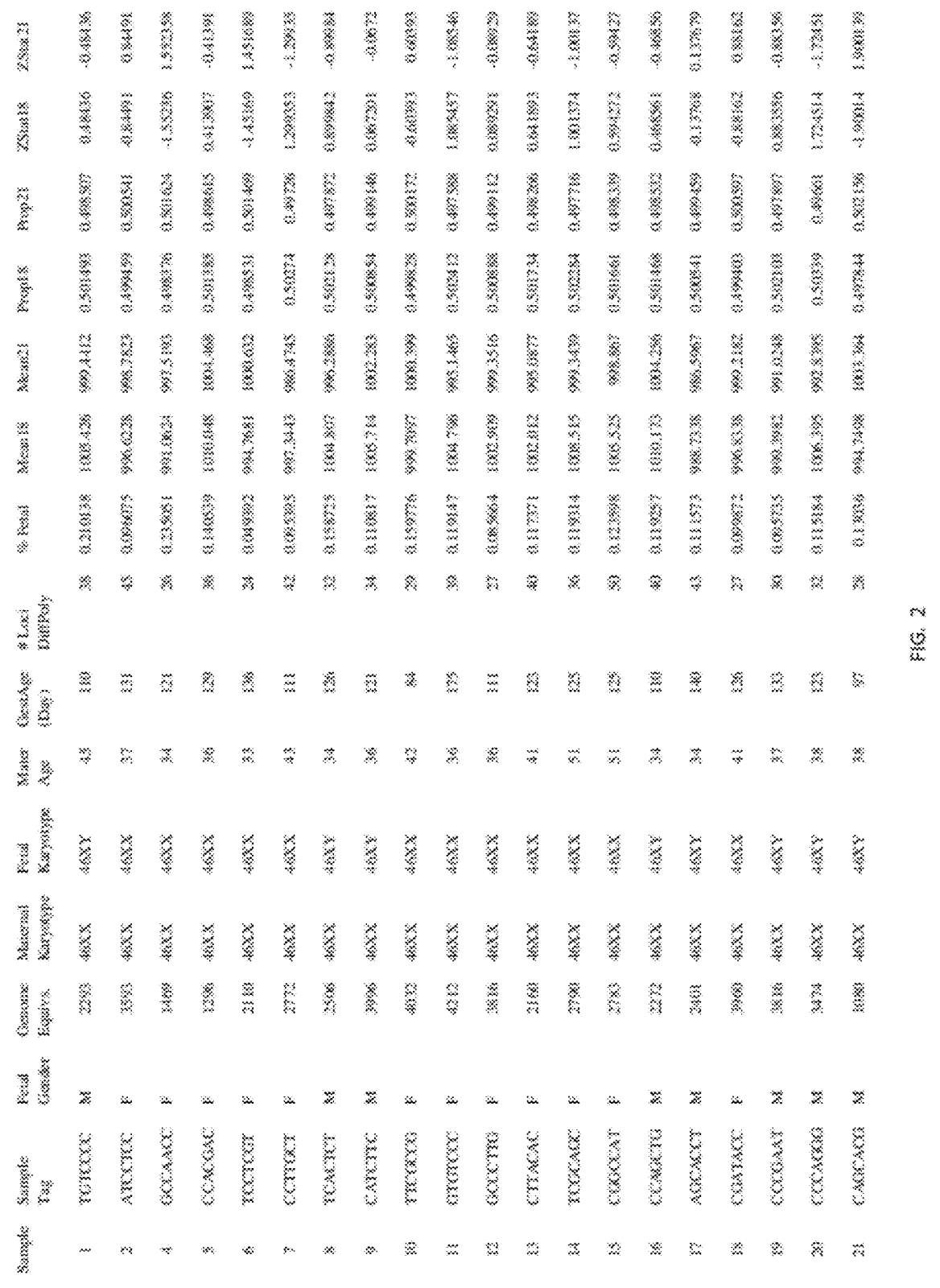
Figure 2:
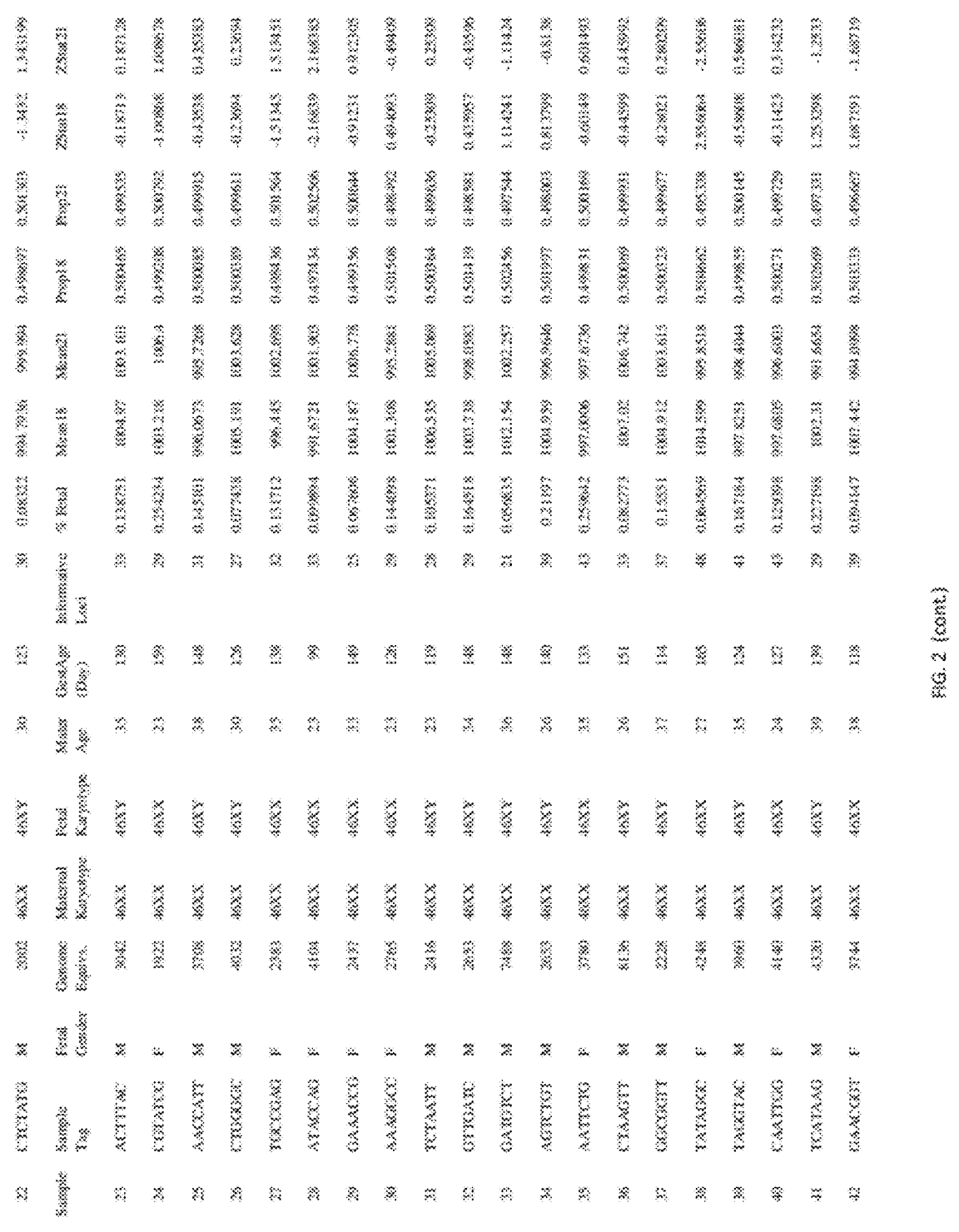
Figure 2:
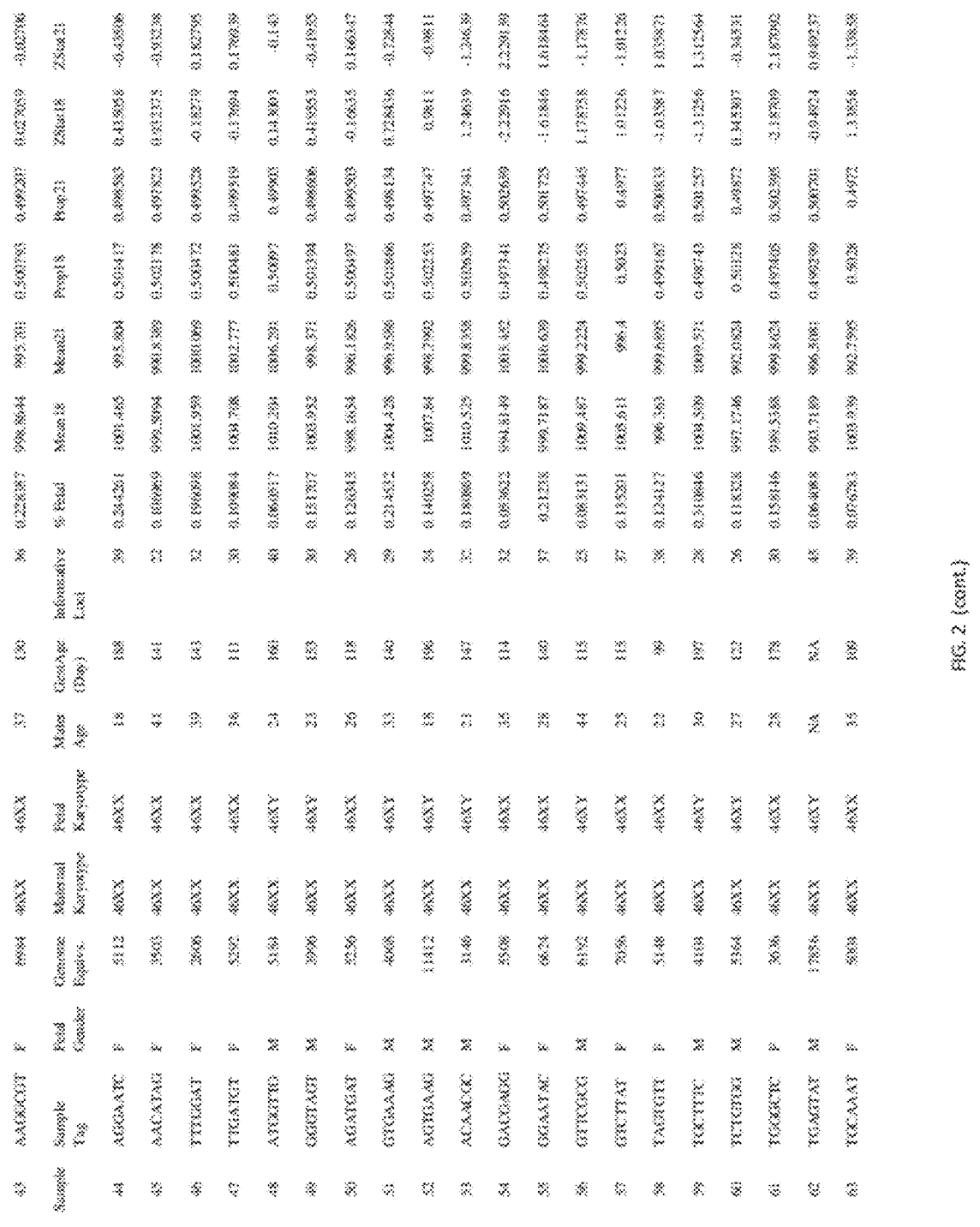
Figure 2:
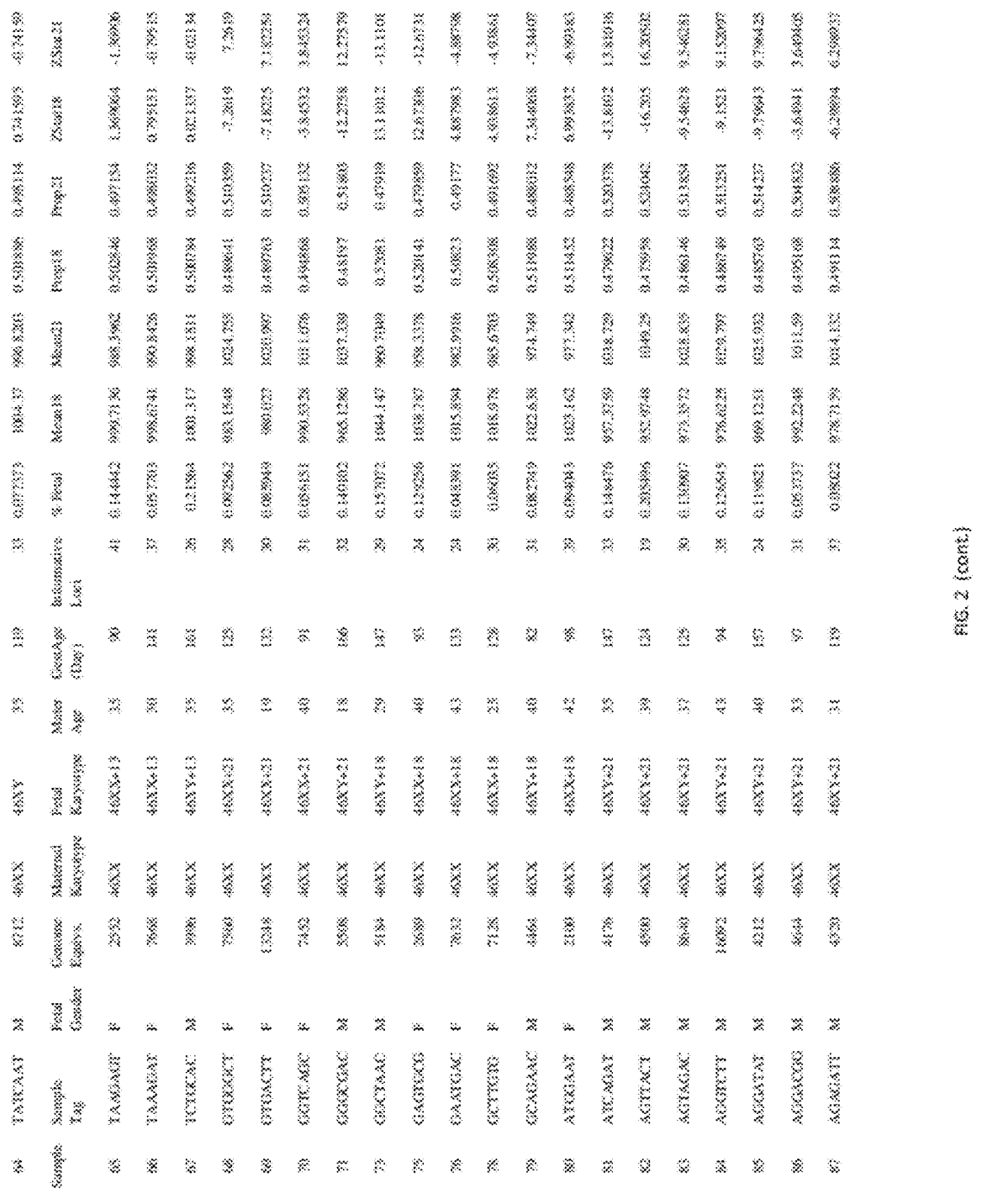
Figure 2:
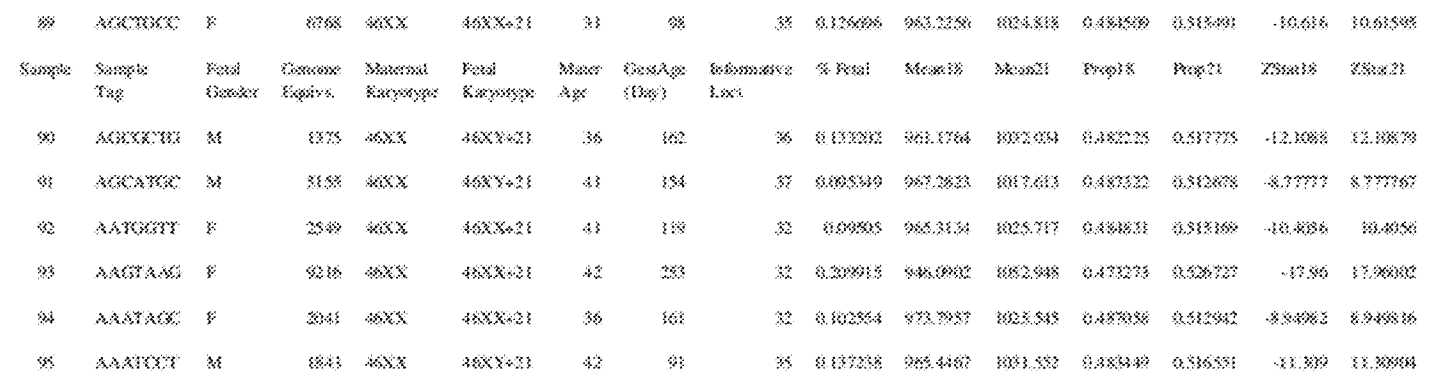

A series of maternal samples, including samples having a trisomy 21 (T21) or trisomy 18 (T18) were interrogated using the techniques described in U.S. Ser. No. 12/013,732. FIG. 2 profiles the demographics of 95 subjects from which maternal samples were obtained and analyzed in this study. The average gestational age for the subjects was 12 weeks, with the average gestational age of the normal, T21, and T18 subjects being 119, 126, and 119 weeks, respectively. The average ages of the subjects from which the normal, T21, and T18 maternal samples were obtained were 31, 34, and 37 years, respectively, presumably reflecting the increased risk of fetal aneuploidy with maternal age.

For each sample analyzed, counts were obtained using the methods described in co-pending application U.S. Ser. No. 12/013,732, which is incorporated herein by reference. A set of 576 loci were selected for chromosome 21 (chr21) and a set of 576 loci were selected for chromosome 18 (chr18), and the overall frequencies of these loci were determined for the maternal samples using amplification and sequencing. Sequence counts for each of these loci were normalized by systematically removing biases introduced by sample and by genomic location using median polish (Tukey, J W. 1977. Exploratory Data Analysis. Reading Massachusetts: Addison-Wesley. Irizarry et al., 2003 Nucleic Acids Res 31(4): e15). The 576 identified loci on each chromosome with the lowest residual variance in counts amongst samples were narrowed to the 384 loci on each chromosome exhibiting the greatest residual difference between normal and trisomy samples using Z statistics derived from individual loci for the test chromosome.

Example 2

Analysis of Non-Polymorphic Loci for Chromosome Proportion

The selected loci were used to compute a chr21 proportion metric for each sample. The mean of counts from the 384 chr21 loci best able to discriminate T21 from normal were divided by the sum of the mean count for the 384 chr21 and mean count for all 576 chr18 loci. A chr18 proportion metric was calculated similarly as the sum of counts from the 384 chr18 loci best able to discriminate T18 from normal divided by the sum of the mean count from all 576 chr21 loci and the mean count for the 384 chr18 loci.

A standard Z test of proportions was used to compute Z statistics:

$$Z_j = \frac{p_j - p_0}{\sqrt{\frac{p_j(1-p_j)}{n_j}}}$$

where $p_j$ is the observed proportion of representation for a given chromosome of interest in a given sample j, $p_0$ is the expected proportion for the given test chromosome calculated as the median $p_j$ and $n_j$ is the mean count for all the chromosomes. Z statistic standardization was performed using iterative censoring. At each iteration, the samples falling outside of three median absolute deviations were removed. After ten iterations, mean and standard deviation were calculated using only the uncensored samples. All samples were then standardized against this mean and standard deviation. The Kolmogorov-Smirnov test (Conover W J. 1971, Practical Nonparametric Statistics. New York: John Wiley & Sons. Pages 295-301) and Shapiro-Wilk's test (Royston P 1982. Applied Statistics 31: 115-124) were used to test for the normality of the normal samples' Z statistics.

Example 3

Figure 3:
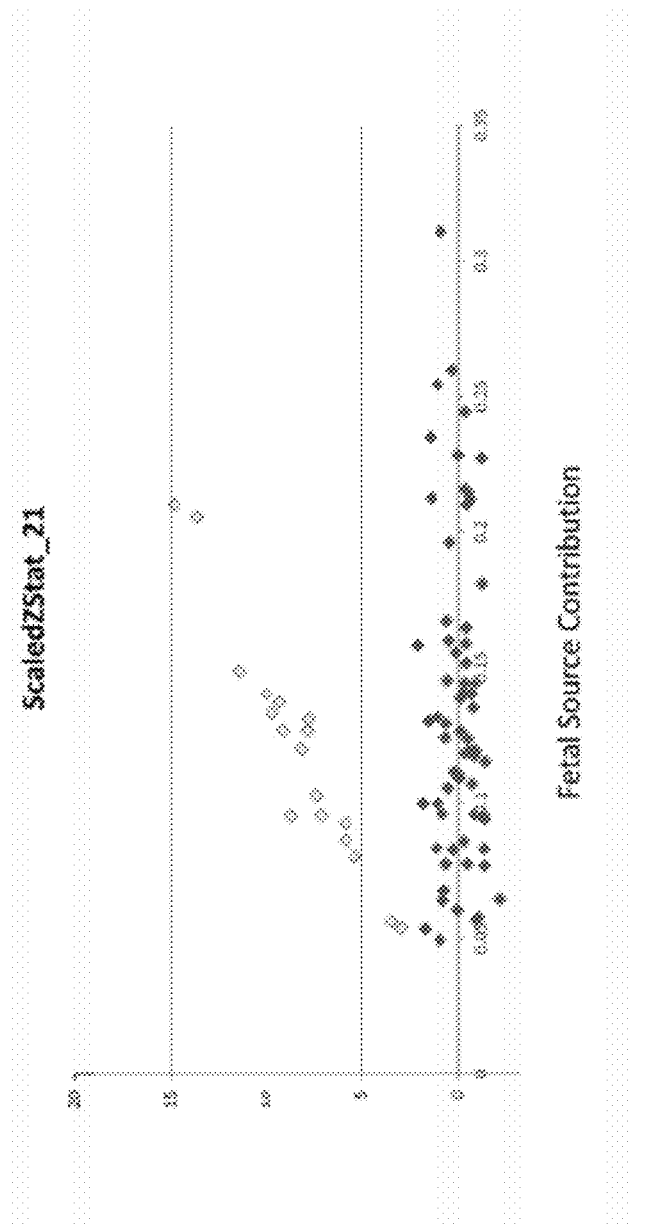
FIG. 3 is a graph illustrating the correlation between fetal source contribution and Z statistic in pregnancies with Trisomy 21.
Figure 4:
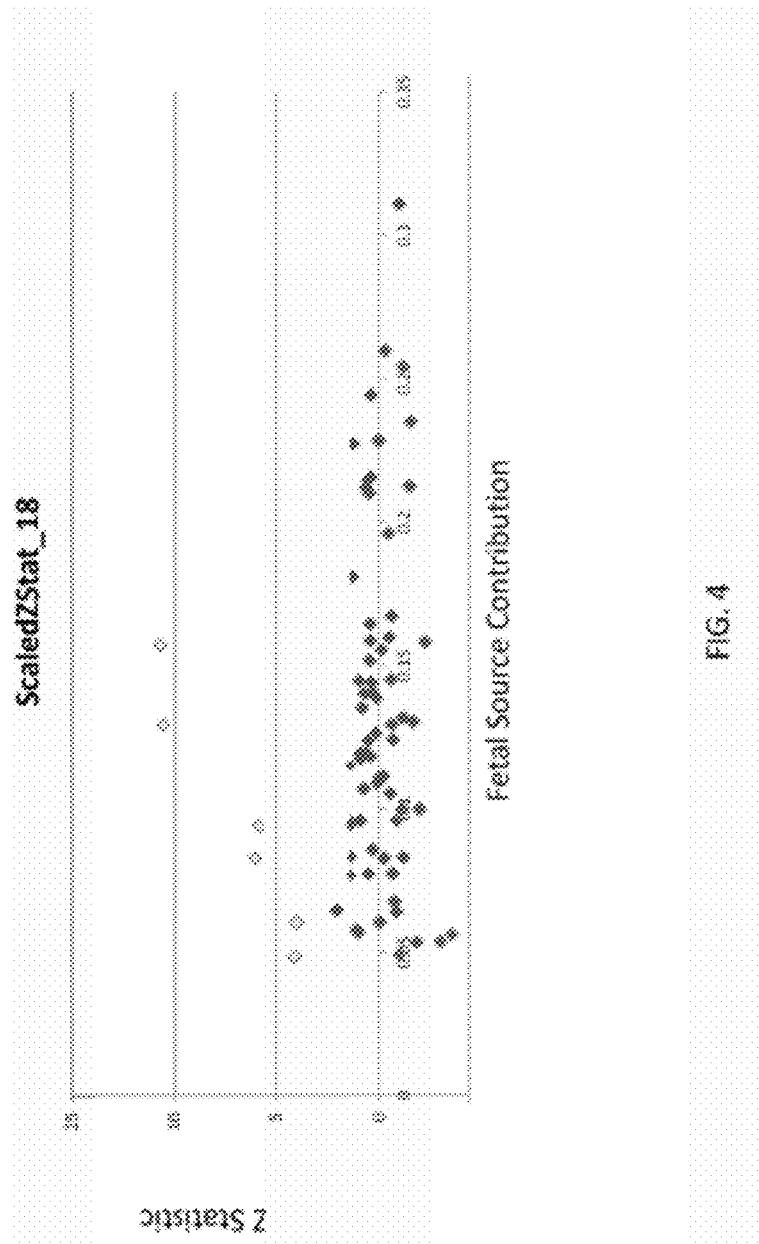
FIG. 4 is a graph illustrating the correlation between fetal source contribution and Z statistic in pregnancies with Trisomy 18.

Analysis of Polymorphic Loci for Determination of Fetal Source Contribution in the Maternal Samples A principal determinant of the scale of response of chromosome proportion to aneuploidy status was based on the fraction of fetal DNA in the sample (fetal source contribution). In order to reliably measure fetal source contribution in a maternal sample regardless of fetal gender, autosomal SNPs were used. The processes utilized did not require prior knowledge of paternal genotype, as the non-maternal alleles were identified during the assay without regard to knowledge of paternal inheritance. Comparative analysis of maternal samples with DNA from male fetuses demonstrated a strong correlation between estimates of fetal contribution using autosomal SNPs and fetal source contribution estimates based upon proportion of counts from chrY loci. Moreover, analysis of pregnancies with aneuploid fetuses demonstrated a strong correlation between fetal source contribution and Z statistic (FIGS. 3 and 4). FIG. 3 shows the correlation demonstrated for Trisomy 21 and FIG. 4 shows the correlation demonstrated for Trisomy 18. The aneuploid samples are shown as light grey diamonds. A maximum likelihood estimate using the binomial distribution was used to calculate the estimated fetal nucleic acid contribution across several informative loci in each maternal sample. The processes for calculation of fetal acid contribution used are described, for example, in U.S. Appln Ser. No. 61/509,188, which is incorporated by reference. The polymorphic regions used for determination of fetal contribution were from chromosomes 1-12, and did not target the blood group antigens. The estimate of fetal contribution from the polymorphic assays was used to define expected response magnitudes when a test chromosome is trisomic, which informed the statistical testing. The test statistic consists of two components: a measure of deviation from the expected proportion when the sample is disomic; and a measure of deviation from the expected proportion when the sample is trisomic. Each component is in the form of a Wald statistic (e.g., Harrell Jr., F E (2001) *Regression modeling strategies*. Springer-Verlag, Sections 9.2.2, 10.5 which compares an observed proportion to an expected proportion and divides by the variation of the observation.

The statistic $W_j$ was used to measure the deviation from expectation when the sample j is disomic, and is defined as $$W_j = \frac{p_j - p_0}{\sigma_{p_j}},$$

The statistic $W_j$ is where $p_j$ and $p_0$ are defined as before with the Z statistic, and $\sigma_{p_j}$ is the standard deviation of the observed proportion of representation for a given chromosome of interest. The standard deviation was estimated using parametric bootstrap sampling to create a distribution of $p_j$ proportions based on the mean counts and standard errors for our chromosomes of interest. The second statistic is $\hat{W}_j$, which replaces $p_0$ with the fetal fraction adjusted reference proportion $\hat{p}_j$ and is defined as $$\hat{p}_j = \frac{(1 + 0.5 f_j) p_0}{((1 + 0.5 f_j) p_0)(1 - p_0)},$$

The statistic $W_j$ is where $f_j$ is the fetal fraction for sample j and $p_0$ is the reference proportion as before. This adjustment accounted for the increased representation of a test chromosome when the fetus was trisomic.

These statistics differ from other Z statistic calculations in that the source of variance comes directly from the observed proportion rather than from the variance around the expected proportion. Because this variance of counts across many loci is measured as a natural result of using multiple non-polymorphic assays for test chromosomes, all estimates were taken within a nascent data set and did not require external reference samples or historical information with normalizing adjustments to control for process drift as is typically required for variance around the expected proportion.

The final statistic used was $S_j = W_j + \hat{W}_j$. Conceptually, deviations from disomic expectation and trisomic expectation were simultaneously evaluated and summarized into this single statistic. The particular advantage of combining these two indicators is that while deviation from disomy might be high, it may not reach the deviation expected for trisomy at a particular fetal contribution level. The $\hat{W}_j$ component will be negative in this case, in effect penalizing the deviation from disomy. An $S_j = 0$ indicated an equal chance of being disomic vs. trisomic.

Example 4

Incorporation of Statistics into Risk Probabilities for Chromosomal Abnormalities The final step of the analysis was to calculate a risk probability score based on the $S_j$. This was accomplished by parametric bootstrapping using standard errors of chromosome count estimates and a fetal source contribution estimate for an individual sample. A risk probability was only calculated for samples having a fetal source contribution of greater than 3.5%.

The standard error of the reference proportion, which was derived using robust estimates in highly multiplexed data sets, was also included in the bootstrapping. From the bootstrap samples, the distribution of S_j was estimated. The odds of trisomy vs. disomy was the proportion of S_j>0 vs. the proportion of S_j≤0.

Example 5

Incorporation of Ancillary Information into Risk Probabilities for Chromosomal Abnormalities In certain aspects, the risk probability is calculated using ancillary information that may change the risk profile of the patient from which the sample was taken. Using Bayesian statistics, a risk probability was calculated that included not only the Wald statistic and proportion of fetal biomolecules present in a maternal sample, but also ancillary information. The exemplary ancillary information used in the risk probability calculation included fetal gestational age (g) and maternal age (m), both of which may affect the risk profile for a fetus being disomic or trisomic at chromosome 21.

The following calculation was used to determine the risk probability of T21:

$$P(T|s,f,g,m) = \frac{P(s|T,f,g,m)P(T,f,g,m)}{P(s|T,f,g,m)P(T,f,g,m) + P(s|D,f,g,m)P(D,f,g,m)}$$

$$P(T,f,g,m) = P(T|f,g,m)P(f,g,m)$$

$$P(D,f,g,m) = P(D|f,g,m)P(f,g,m)$$

where T=the probability that the fetus is trisomic, D is the probability that the fetus is disomic at chromosome 21, s is the calculated Wald statistic (as described in Example 4), f is percentage of fetal DNA in the sample, g is gestational age of the fetus, and m is the maternal age.

Assuming that the detected fetal contribution in a sample was independent of trisomy status, as evidenced by previous empirical evidence that failed to identify a correlation between trisomy and fetal DNA proportion in a maternal sample (not shown), the following assumptions were made:

$$P(T|f,g,m) \cong P(T|g,m)$$

$$P(D|f,g,m) \cong P(D|g,m)$$

Assuming s is independent of g and/or m:

$$P(s|T,f,g,m) = P(s|T,f)$$

the risk probability of T21 in a fetus was calculated by the following equation:

$$P(T|s,f,g,m) = \frac{P(s|T,f)P(T|g,m)}{P(s|T,f)P(T|g,m) + P(s|D,f)P(D|g,m)}$$

While this invention is satisfied by aspects in many different forms, as described in detail in connection with preferred aspects of the invention, it is understood that the present disclosure is to be considered as exemplary of the principles of the invention and is not intended to limit the invention to the specific aspects illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. §112, ¶6.

What is claimed is:

1. A computer-implemented process for calculating risk probabilities for fetal aneuploidies in a maternal sample, wherein at least one processor coupled to a memory executes a software component that performs the process comprising:
    determining a frequency of a first set of at least twelve or more non-polymorphic loci from a first chromosome in the maternal sample;
    determining a frequency of a second set of at least twelve or more non-polymorphic loci from a second chromosome in the maternal sample;
    determining the frequency of a third set of at least twelve or more polymorphic loci from one or more chromosomes other than the first and second chromosome in the maternal sample;
    determining an overall frequency of the non-polymorphic and polymorphic loci;
    computing a chromosome proportion metric for the first and second chromosome in the maternal sample using the overall frequency of the non-polymorphic loci;
    comparing the frequency of the polymorphic loci to determine a percent fetal nucleic acid in the maternal sample;
    for each first and second chromosome, measuring a deviation from an expected chromosome proportion metric when a chromosome is euploid;
    for each first and second chromosome, measuring a deviation from an expected chromosome proportion metric when a chromosome is aneuploid using the computed percent fetal nucleic acid in the maternal sample; and
    calculating an initial risk probability score for the maternal sample based on the deviations from the expected chromosome proportion metrics for the first and second chromosomes.

2. The process of claim 1, wherein the maternal sample is maternal blood, maternal plasma or maternal serum.

3. The process of claim 1, wherein the maternal sample is maternal plasma.

4. The process of claim 1, wherein the frequencies of the non-polymorphic and polymorphic loci are determined by sequencing.

5. The process of claim 4, wherein the non-polymorphic and polymorphic loci are preselected through sequence-specific amplification of loci prior to sequencing.

6. The process of claim 4, wherein the frequencies of the non-polymorphic and polymorphic loci are determined through massively parallel shotgun sequencing.

7. The process of claim 1, wherein the frequencies of the non-polymorphic and polymorphic loci are determined using digital PCR.

8. The process of claim 1, further comprising adjusting the calculated initial risk probability using ancillary information.

9. The process of claim 8, wherein the ancillary information is maternal age.

10. The process of claim 8, wherein the ancillary information is gestational age.

11. The process of claim 8, wherein the ancillary information is results from a prior medical test or procedure.

* * * * *